(12) United States Patent
Retting et al.

(10) Patent No.: US 12,037,603 B2
(45) Date of Patent: Jul. 16, 2024

(54) METHODS FOR TISSUE FABRICATION

(71) Applicant: Organovo, Inc., San Diego, CA (US)

(72) Inventors: Kelsey Nicole Retting, San Diego, CA (US); Deborah Lynn Greene Nguyen, San Diego, CA (US); Sharon C. Presnell, Poway, CA (US); Shelby Marie King, San Diego, CA (US)

(73) Assignee: Organovo, Inc., San Diego, CA (US)

( * ) Notice: Subject to any disclaimer, the term of this patent is extended or adjusted under 35 U.S.C. 154(b) by 0 days.

(21) Appl. No.: 17/491,862

(22) Filed: Oct. 1, 2021

(65) Prior Publication Data

US 2022/0195380 A1    Jun. 23, 2022

Related U.S. Application Data

(63) Continuation of application No. 15/765,110, filed as application No. PCT/US2016/061156 on Nov. 9, 2016, now abandoned, which is a continuation of application No. 14/936,580, filed on Nov. 9, 2015, now abandoned.

(60) Provisional application No. 62/253,064, filed on Nov. 9, 2015.

(51) Int. Cl.
| | |
|---|---|
| *C12N 5/00* | (2006.01) |
| *B29C 64/112* | (2017.01) |
| *B33Y 70/00* | (2020.01) |
| *B33Y 80/00* | (2015.01) |
| *B41J 2/01* | (2006.01) |
| *C12N 5/071* | (2010.01) |
| *C12N 5/077* | (2010.01) |
| *B29L 31/00* | (2006.01) |

(52) U.S. Cl.
CPC .......... *C12N 5/0068* (2013.01); *B29C 64/112* (2017.08); *B33Y 70/00* (2014.12); *B33Y 80/00* (2014.12); *B41J 2/01* (2013.01); *C12N 5/0062* (2013.01); *C12N 5/0656* (2013.01); *C12N 5/0697* (2013.01); *B29L 2031/7532* (2013.01); *C12N 2502/091* (2013.01); *C12N 2502/094* (2013.01); *C12N 2523/00* (2013.01); *C12N 2533/54* (2013.01); *C12N 2539/00* (2013.01)

(58) Field of Classification Search
None
See application file for complete search history.

(56) References Cited

U.S. PATENT DOCUMENTS

| | | | |
|---|---|---|---|
| 4,759,764 A | 7/1988 | Fawcett et al. | |
| 4,808,435 A | 2/1989 | Cropp et al. | |
| 5,099,090 A | 3/1992 | Allan et al. | |
| 6,315,469 B1 | 11/2001 | Alvarez et al. | |
| 6,401,795 B1 | 6/2002 | Cesarano, III et al. | |
| 6,454,972 B1 | 9/2002 | Morisette et al. | |
| 6,520,997 B1 | 2/2003 | Pekkarinen et al. | |
| 6,537,567 B1 | 3/2003 | Niklason et al. | |
| 6,561,607 B1 | 5/2003 | Lubinsky et al. | |
| 6,642,243 B1 | 11/2003 | Imanzahrai | |
| 6,713,772 B2 | 3/2004 | Goodman et al. | |
| 6,939,489 B2 | 9/2005 | Moszner et al. | |
| 6,942,830 B2 | 9/2005 | Muelhaupt et al. | |
| 6,979,670 B1 | 12/2005 | Lyngstadaas et al. | |
| 6,986,739 B2 | 1/2006 | Warren et al. | |
| 7,051,654 B2 | 5/2006 | Boland et al. | |
| 7,196,842 B2 | 3/2007 | Weigl et al. | |
| 7,484,837 B2 | 2/2009 | Koga et al. | |
| 7,625,198 B2 | 12/2009 | Lipson et al. | |
| 7,651,665 B2 | 1/2010 | Gonzalez et al. | |
| 7,680,555 B2 | 3/2010 | Dunn et al. | |
| 7,767,446 B2 | 8/2010 | Robbins et al. | |
| 8,143,055 B2 | 3/2012 | Forgacs et al. | |
| 8,241,905 B2 | 8/2012 | Forgacs et al. | |
| 8,343,740 B2 | 1/2013 | Gonda et al. | |
| 8,580,546 B2 | 11/2013 | Gonda et al. | |
| 8,728,807 B2 | 5/2014 | Forgacs et al. | |
| 8,747,880 B2 | 6/2014 | Forgacs et al. | |
| 8,852,932 B2 | 10/2014 | Forgacs et al. | |
| 8,931,880 B2 | 1/2015 | Murphy et al. | |
| 9,149,952 B2 | 10/2015 | Murphy et al. | |
| 9,855,369 B2 | 1/2018 | Murphy et al. | |
| 2001/0042942 A1 | 11/2001 | Hizumi et al. | |
| 2002/0171178 A1 | 11/2002 | Dean et al. | |
| 2002/0182633 A1 | 12/2002 | Chen et al. | |
| 2002/0188349 A1 | 12/2002 | McAllister et al. | |
| 2003/0049839 A1 | 3/2003 | Romero-Ortega et al. | |
| 2003/0149505 A1 | 8/2003 | Mogensen | |

(Continued)

FOREIGN PATENT DOCUMENTS

| | | |
|---|---|---|
| CA | 2306346-A1 | 1/1999 |
| EP | 2090584 A1 | 8/2009 |

(Continued)

OTHER PUBLICATIONS

Iwami, K., et al., "Bio rapid prototyping by extruding/aspirating/refilling thermoreversible hydrogel," *Biofabrication* 2(1):014108, IOP Publishing Ltd., United Kingdom (2010).

Office Action dated Nov. 2, 2016, in U.S. Appl. No. 14/936,580, Retting, K.N., et al., filed Nov. 9, 2015, 15 pages.

Office Action dated Jun. 1, 2017, in U.S. Appl. No. 14/936,580, Retting, K.N., et al., filed Nov. 9, 2015, 26 pages.

(Continued)

*Primary Examiner* — Emily A Cordas

(74) *Attorney, Agent, or Firm* — STERNE, KESSLER, GOLDSTEIN & FOX P.L.L.C.

(57) ABSTRACT

Disclosed herein are improved methods for fabricating bioprinted, three-dimensional, biological tissues. The methods relate to exposures to low temperatures, incubations at low temperatures of various durations, and fabrication in environments without structural cross-linking treatments.

17 Claims, 18 Drawing Sheets

(5 of 18 Drawing Sheet(s) Filed in Color)

(56) References Cited

U.S. PATENT DOCUMENTS

| | | |
|---|---|---|
| 2003/0153078 A1 | 8/2003 | Libera et al. |
| 2003/0175410 A1 | 9/2003 | Campbell et al. |
| 2003/0236588 A1 | 12/2003 | Jang et al. |
| 2004/0006405 A1 | 1/2004 | Chen et al. |
| 2004/0132184 A1 | 7/2004 | Dennis et al. |
| 2004/0197367 A1 | 10/2004 | Rezania et al. |
| 2004/0219133 A1 | 11/2004 | Lyles |
| 2004/0253365 A1 | 12/2004 | Warren et al. |
| 2005/0009178 A1 | 1/2005 | Yost et al. |
| 2005/0169962 A1 | 8/2005 | Bhatia et al. |
| 2005/0226856 A1 | 10/2005 | Ahlfors |
| 2005/0276791 A1 | 12/2005 | Hansford et al. |
| 2006/0099287 A1 | 5/2006 | Kim et al. |
| 2006/0198918 A1 | 9/2006 | Koyagi et al. |
| 2006/0237880 A1 | 10/2006 | Wicker et al. |
| 2006/0270032 A1 | 11/2006 | Bhatia et al. |
| 2007/0142916 A1 | 6/2007 | Olson et al. |
| 2007/0200276 A1 | 8/2007 | Mackey et al. |
| 2007/0231787 A1 | 10/2007 | Voelker |
| 2007/0299508 A1 | 12/2007 | Morrison et al. |
| 2008/0027114 A1 | 1/2008 | Funke et al. |
| 2008/0097575 A1 | 4/2008 | Cottone |
| 2008/0192074 A1 | 8/2008 | Dubois et al. |
| 2008/0193910 A1 | 8/2008 | Larkin et al. |
| 2009/0076531 A1 | 3/2009 | Richardson et al. |
| 2009/0117087 A1 | 5/2009 | Carroll et al. |
| 2009/0142307 A1 | 6/2009 | Athanasiou et al. |
| 2009/0206522 A1 | 8/2009 | Hein et al. |
| 2009/0208466 A1 | 8/2009 | Yoo et al. |
| 2009/0208577 A1 | 8/2009 | Xu et al. |
| 2009/0239302 A1 | 9/2009 | Decher et al. |
| 2009/0248145 A1 | 10/2009 | Chan et al. |
| 2009/0267269 A1 | 10/2009 | Lim et al. |
| 2010/0056390 A1 | 3/2010 | Fischbach |
| 2010/0145469 A1 | 6/2010 | Barralet et al. |
| 2010/0160183 A1 | 6/2010 | Xu et al. |
| 2010/0191360 A1 | 7/2010 | Napadensky et al. |
| 2010/0254900 A1 | 10/2010 | Campbell et al. |
| 2011/0064784 A1 | 3/2011 | Mullens et al. |
| 2011/0172611 A1 | 7/2011 | Yo et al. |
| 2011/0180914 A1 | 7/2011 | Do et al. |
| 2011/0212501 A1 | 9/2011 | Yoo |
| 2011/0250688 A1 | 10/2011 | Hasan |
| 2012/0045770 A1 | 2/2012 | Pongracz et al. |
| 2012/0089238 A1 | 4/2012 | Kang et al. |
| 2012/0116568 A1 | 5/2012 | Murphy et al. |
| 2013/0108726 A1 | 5/2013 | Uckelmann et al. |
| 2013/0164339 A1 | 6/2013 | Murphy et al. |
| 2013/0190210 A1 | 7/2013 | Murphy et al. |
| 2013/0193619 A1 | 8/2013 | Church et al. |
| 2013/0236431 A1 | 9/2013 | Gourdie et al. |
| 2013/0236879 A1 | 9/2013 | Berry et al. |
| 2013/0345794 A1 | 12/2013 | Khatiwala et al. |
| 2014/0012225 A1 | 1/2014 | Yoo et al. |
| 2014/0044822 A1 | 2/2014 | Mulliken |
| 2014/0093932 A1 | 4/2014 | Murphy et al. |
| 2014/0099709 A1 | 4/2014 | Presnell et al. |
| 2014/0131313 A1 | 5/2014 | Wakamatsu et al. |
| 2014/0220685 A1 | 8/2014 | Forgacs et al. |
| 2014/0265049 A1 | 9/2014 | Burris et al. |
| 2014/0274802 A1 | 9/2014 | Shepherd et al. |
| 2014/0287960 A1 | 9/2014 | Shepherd et al. |
| 2014/0358273 A1 | 12/2014 | Labossiere et al. |
| 2015/0004273 A1 | 1/2015 | Forgacs et al. |
| 2015/0037445 A1 | 2/2015 | Murphy et al. |
| 2015/0057786 A1 | 2/2015 | Murphy et al. |
| 2015/0282885 A1 | 10/2015 | King et al. |
| 2015/0314613 A1 | 11/2015 | Murphy et al. |
| 2015/0344828 A1 | 12/2015 | Forgacs et al. |
| 2016/0097039 A1 | 4/2016 | Nguyen et al. |
| 2016/0122723 A1 | 5/2016 | Retting et al. |

FOREIGN PATENT DOCUMENTS

| | | |
|---|---|---|
| EP | 2679669 A1 | 1/2014 |
| JP | 2001038981 A | 2/2001 |
| JP | 2005031144 A | 2/2005 |
| JP | 2006159117 A | 6/2006 |
| KR | 20090087748 A | 8/2009 |
| RU | 2371758 C2 | 10/2009 |
| WO | WO-9901538 A | 1/1999 |
| WO | WO-2001068811 A2 | 9/2001 |
| WO | WO-2004108418 A1 | 12/2004 |
| WO | WO-2005025493 A2 | 3/2005 |
| WO | WO-2005081970 A2 | 9/2005 |
| WO | WO-2007076272 A2 | 7/2007 |
| WO | WO-2007115336 A2 | 10/2007 |
| WO | WO-2007115337 A2 | 10/2007 |
| WO | WO-2007124023 A2 | 11/2007 |
| WO | WO-2007125893 A1 | 11/2007 |
| WO | WO-2007126411 A2 | 11/2007 |
| WO | WO-2007136936 A2 | 11/2007 |
| WO | WO-2009102484 A2 | 8/2009 |
| WO | WO-2009154466 A1 | 12/2009 |
| WO | WO-2010008905 A2 | 1/2010 |
| WO | WO-2011038373 A2 | 3/2011 |
| WO | WO-2011088213 | 7/2011 |
| WO | WO-2011097330 A2 | 8/2011 |
| WO | WO-2011107599 A1 | 9/2011 |
| WO | WO-2011119059 A1 | 9/2011 |
| WO | WO-2012003465 A2 | 1/2012 |
| WO | WO-2012054195 A2 | 4/2012 |
| WO | WO-2012131000 A1 | 10/2012 |
| WO | WO-2013130823 A1 | 9/2013 |
| WO | WO-2013192290 A1 | 12/2013 |
| WO | WO-2014151921 A1 | 9/2014 |
| WO | WO-2015066705 A1 | 5/2015 |
| WO | WO-2015069619 A1 | 5/2015 |

OTHER PUBLICATIONS

Supplementary European Search Report for EP Application No. EP 16 86 4922, Munich, Germany, dated Mar. 19, 2019, 8 pages.

Gupta, S., et al., "Evolution of PVA gels prepared without crosslinking agents as a cell adhesive surface," *J Mater Sci: Mater Med* 22:1763-1772, Springer Science+Business Media, LLC, United States (2011).

Kagan, R.J., et al., "Human Skin Banking," *Clin. Lab. Med.* 25:587-605, Elsevier Inc., Netherlands (2005).

Nicodemus, G.D. and Bryant, S.J., "Cell Encapsulation in Biodegradable Hydrogels for Tissue Engineering Applications," *Tissue Engineering: Part B* 14:149-165, Mary Ann Liebert, United States (2008).

International Search Report for International Application No. PCT/US2016/61156, United States Patent and Trademark Office, United States dated Jan. 24, 2017, 2 pages.

ATCC Product Catalog MCF7 (Atcc® HTB-22TM), accessed at https://www.atcc.org/products/all/HTB-22.aspx?slp=1#generalinformation, accessed on Sep. 18, 2015.

ATCC Product catalog Primary Subcutaneous Pre-adipocytes; Normal, Human (Atcc® PCS-210-01OTM), accessed at https://www.atcc.org/Products/AII/PCS-210-O1O.aspx?slp=1, accessed on Sep. 18, 2015.

Baltich, J., et al., "Development of a Scaffoldless Three-Dimensional Engineered Nerve Using a Nerve-Fibroblast Co-Culture," *In Vitro Cell. Dev. Biol.—Animal* 46:438-444, Springer Science+Business Media, LLC, United States (2010).

Bioscaffolder 2008, www.syseng.de, SYSENG Dipl.-lng. Hendrik John.

Boland, T., et al., "Application of inkjet printing to tissue engineering," *Biotech J.* 1:910-917, Wiley, United States (2006).

Boland, T., et al., "Cell and Organ Printing 2: Fusion of Cell Aggregates in Three-Dimensional Gels," *The Anatomical Record, Part A.* 272A:497-502, Wiley, United States (2003).

Bunnell B., et al., "Adipose-derived Stem Cells: Isolation, Expansion and Differentiation," *Methods* 45(2):115-120, Elsevier, Netherlands (2008).

(56) References Cited

OTHER PUBLICATIONS

Chaterji, S., et al., "Scaffold-Free In Vitro Arterial Mimetics: The Importance of Smooth Muscle- Endothelium Contact," *Tissue Engineering: Part A* 16(8):1901-1912, Mary Ann Liebert, United States (2010).

Sciperio, Inc. 2003 R&D 100 Award Winner. Sciperio, http://www.sciperio.com/news/20031016.asp, accessed on Feb. 1, 2005, 2 pages.

Constans. Body by Science. The Scientist 17(19):34-37 http://www.the-scientist.com/article/display/141541 (2003).

Cui, X., et al., "Direct Human Cartilage Repair Using Three-Dimensional Bioprinting Technology," *Tissue Engineering Part A* 18(11-12): 1304-1312, Mary Ann Liebert, United States (2012).

Dai, W., et al., "Fibroblast Aggregation by Suspension with Conjugates of Poly(ethylene glycol) and RGD.," *Biotechnology and Bioengineering* 50(4):349-356, Wiley, United States (May 1996).

Dirat, B., et al., "Cancer-associated adipocytes exhibit an activated phenotype and contribute to breast cancer invasion," *Cancer Res.* 71(7):2455-2465, American Association for Cancer Research, United States (2011).

Dominici, M., et al., "Minimal criteria for defining multipotent mesenchymal stromal cells. International Society for Cellular Therapy position statement," *Cytotherapy* 8(4):315-317, Elsevier, United States (2006).

Edelman, E.R., "Vascular Tissue Engineering: Designer Arteries," *Circ Res.* 85(12):1115-1117, Lippincot Williams and Wilkins, United States (1999).

Egebald, M., et al., "Tumors as organs: complex tissues that interface with the entire organism," *Dev Cell.* 18(6):884-901, Elsevier, United States (2010).

Eisenberg, C., et al., "Bone Marrow Cells Transdifferentiate to Cardiomyocytes When Introduced into the Embryonic Heart," *Stem Cells* 24:1236-1245, Oxford Press, United Kingdom (2006).

Fedorovich, N., et al., "Distinct Tissue Formation by Heterogeneous Printing of Osteo- and Endothelial Progenitor Cells," *Tissue Engineering: Part A* 17(15-16):2113-2123, Mary Ann Liebert, United States (2011).

Fedorovich, N., et al., "Three-Dimensional Fiber Deposition of Cell-Laden, Viable Patterned Constructs for Bone Tissue Printing," *Tissue Engineering: Part A* 14(1):127-135, Mary Ann Liebert, United States (2008).

Forgacs, G., et al., Biological Relevance of Tissue Liquidity and Viscoelasticity, Eds. A. Deutsch, M. Falcke, J. Howard and W. Zimmermann. Birkhauser. pp. 269-277 (2004).

Forgacs, G., et al., "Viscoelastic Properties of Living Embryonic Tissues: A Quantitative Study," *Biophysical Journal* 74(5):2227-2234, Elsevier, United States (May 1998).

Foty, R.A., et al., "Surface Tensions of Embryonic Tissues Predict Their Mutual Envelopment Behavior," *Development* 122(5):1611-1620, The Company of Biologists, United Kingdom (1996).

Foty, R.A., et al., "The Differential Adhesion Hypothesis: A Direct Evaluation," *Developmental Biology* 278(1):255-263, Elsevier, Netherlands (2005).

Frisman, I., et al., "Nanostructuring of PEG-fibrinogen polymeric scaffolds," *Acta Biomaterialia* 6(7):2518-2524, Elsevier, Netherlands (2009).

Fuellhase, C., et al., "264 Generation of Organized Bladder Tissue Constructs Using a Novel Hybrid Printing System," *European Urology Supplements* 8(4):186, Elsevier, Netherlands (2009).

Furukawa, K., et al., "Formation of Human Fibroblast Aggregates (Spheroids) by Rotational Culture," *Cell Transplantation* 10(4-5):441-445, SAGE Publications, United States (2001).

Furukawa, K., et al., Scaffold-free cartilage tissue by mechanical stress loading for tissue engineering. In Tissue Engineering, Ed. D. Eberli, InTech p. 409-428 (2010).

Furukawa, K., et al., "Tissue-engineered Skin Using Aggregates of Normal Human Skin Fibroblasts and Biodegradable Material," *Journal of Artificial Organs* 4:353-356, Springer, United Kingdom (2001).

Ghorbanian, S., et al., "Microfluidic direct writer with integrated declogging mechanism for fabricating cell-laden hydrogel constructs," *Biomed Microdevices* 16:387-395, Springer Science+Business Media, United States (2014).

Glazier, J.A., et al., "Simulation of the Differential Adhesion Driven Rearrangement of Biological Cells," *Physical Review E* 47(3):2128-2154, American Physical Society, United States (Mar. 1993).

Glicklis, R., et al., "Modeling Mass Transfer in Hepatocyte Spheroids via Cell Viability, Spheroid Size, and Hepatocellular Functions," *Biotechnology and Bioengineering* 86(6):672-680, Wiley, United States (Jun. 2004).

Graner, F., et al., "Simulation of Biological Cell Sorting Using a Two-Dimensional Extended Potts Model," *Physical Review Letters* 69(13):2013-2016, American Physical Society, United Staets (Sep. 1992).

Grange, C., et al., "Isolation and characterization of human breast tumor-derived endothelial cells," *Oncol Rep.* 15(2):381-386, Spandidos Publications, Greece (2006).

Gruene, M., et al., "Laser Printing of Stem Cells for Biofabrication of Scaffold-Free Autologous Grafts," *Tissue Engineering: Part C* 17(1):79-89, Mary Ann Liebert, United States (2011).

Gruene, M., et al., "Laser printing of three-dimensional multicellular arrays for studies of cell-cell and cell-environment interactions," *Tissue Eng Part C Methods* 17(10):973-82, Mary Ann Liebert, United States (2011).

Guenard, V., et al., "Syngeneic Schwann Cells Derived from Adult Nerves Seeded in Semipermeable Guidance Channels Enhance Peripheral Nerve Regeneration," *The Journal of Neuroscience* 12(9):3310-3320, Society for Neuroscience, United States (Sep. 1992).

Guillemot, F., et al., "High-throughput laser printing of cells and biomaterials for tissue engineering," *Acta biomaterialia* 6:2494-2500, Elsevier, Netherlands (2010).

Hadlock, T., et al., "A Polymer Foam Conduit Seeded with Schwann Cells Promotes Guided Peripheral Nerve Regeneration," *Tissue Engineering* 6(2):119-127, SAGE Publications, United States (2000).

Halley, et al., Growing Organs in the Lab. Longevity. 1-7 (Jun. 2009).

Harvey, T., et al., "Schwann cells and fetal tectal tissue cografted to the midbrain of newborn rats: fate of Schwann cells and their influence on host retinal innervation of grafts," *Exp Neurol.* 134(2):179-91, Elsevier, Netherlands (1995).

Hockaday, L.A., et al., "Rapid 3D printing of anatomically accurate and mechanically heterogeneous aortic valve hydrogel scaffolds," *Biofabrication* 4(3):1-12, IOP Publishing, United Kingdom (2012).

Hubbard, et al. Bioengineered, Autologous, Scaffold-free Nerve Conduit for Peripheral Nerve Repair. Abstract. AAHS/ASPN/ASRM 2011, Annual Scientific Meetings Program Book. pp. 140 and 159 (Jan. 12-18, 2011).

Ito, A., et al., "Novel Methodology for Fabrication of Tissue-Engineered Tubular Constructs Using Magnetite Nanoparticles and Magnetic Force," *Tissue Engineering* 11(9-10):1553-1561, SAGE Publications, United States (2005).

Iwasaki, K., et al., "Bioengineered Three-Layered Robust and Elastic Artery Using Hemodynamically-Equivalent Pulsatile Bioreactor," *Circulation* 18(14 Suppl):S53-S57, Lippincott Williams & Wilkins, United States (2008).

Izaguirre, J., et al., "CompuCell, a multi-model framework for simulation of morphogenesis," *Bioinformatics* 20(7):1129-1137, Oxford University Press, United Kingdom (2004).

Jakab, K., et al., "Engineering Biological Structures of Prescribed Shape Using Self-assembling Multicellular Systems," *PNAS USA* 101:2864-2869, National Academy of Sciences, United States (2004).

Jakab, K., et al., "Organ printing: fiction or science," *Biorheology* 43(3-4):371-375, IOS Press, Netherlands (2004).

Jakab, K., et al., "Relating Cell and Tissue Mechanics: Implications and Applications," *Developmental Dynamics* 237:2438-2449, Wiley, United States (2008).

Jakab, K., et al., "Three-dimensional tissue constructs built by bioprinting," *Biorheology* 43(3-4):509-513, IOS Press, Netherlands (2006).

Jakab, K., et al., "Tissue Engineering by Self-Assembly and Bio-printing of living cells," *Biofabrication* 2(2):022001, IOP Publishing, United Kingdom (Jun. 2010).

(56) References Cited

OTHER PUBLICATIONS

Jakab, K., et al., "Tissue Engineering by Self-Assembly of Cells Printed into Topologically Defined Structures," *Tissue Engineering: Part A.* 14:413-421, Mary Ann Liebert, United States (2008).

Kasko. Degradable Poly(ethylene glycol) Hydrogels for 2D and 3D Cell Culture. Aldrich Materials Science, pp. 67-75 (no date available).

Kelm, J., et al. "Design of Custom-Shaped Vascularized Tissues Using Microtissue Spheroids as Minimal Building Units," *Tissue Engineering* 12(8):2151-2160, Mary Ann Liebert, United States (2006).

Kelm, J., et al., "Microscale Tissue Engineering Using Gravity-Enforced Cell Assembly," *Trends in Biotechnology* 22(4):195-202, Elsevier, Netherlands (Apr. 2004).

Khatiwala, C., et al., "3D Cell Bioprinting for Regenerative Medicine Research and Therapies," *Gene Therapy and Regulation* 7(1):1-19 (2012).

King et al. Development of 3D bioprinted human breast cancer for in vitro screening of therapeutics targeted against cancer progression. IEEE The American Society for Cell biology. 2013 ASCB annual meeting. New Orleans: IEEE Dec. 14-18, 2013.

Koibuchi, N., et al., "Behavior of Cells in Artificially Made Cell Aggregates and Tissue Fragments after Grafting to Developing Hind Limb Buds in Xenopus laevis," *The International Journal of Developmental Biology* 43(2):141-148, University of the Basque Country Press, Spain (1999).

Korff, T., et al., "Blood Vessel Maturation in a 3-Dimensional Spheroidal Coculture Model: Direct Contact with Smooth Muscle Cells Regulates Endothelial Cell Quiescence and Abrogates VEGF Responsiveness," *The FASEB Journal* 15:447-457, Federation of American Societies for Experimental Biology, United States (Feb. 2001).

Larkin, L., et al., "Structure and Functional Evaluation of Tendon-Skeletal Muscle Constructs Engineered in Vitro," *Tissue Eng.* 12(11):3149-3158, Mary Ann Liebert, United States (2006).

Lee, W., et al., "Multi-layered Culture of Human Skin Fibroblasts and Keratinocytes Through Three-dimensional Freeform Fabrication," *Biomaterials* 30:1587-1595, Elsevier, Netherlands (2009).

L'Heureux, N., et al., "A completely biological tissue-engineered human blood vessel," *The FASEB Journal* 12(1):47-56, Federation of American Societies for Experimental Biology, United States (1998).

L'Heureux, N., et al., "Human tissue-engineered blood vessels for adult arterial revascularization," *Nature Medicine* 12(3):361-365, Springer, Germany (2006).

L'Heureux, N., et al., "Sheet-Based Tissue Engineering From Bench Top to the First Clinical Use of a Completely Biological Tissue Engineered Vessel," *The FASEB Journal* 12(1):47-56, Federation of American Societies for Experimental Biology, United States (2006).

Luo, Y., et al., "Three-dimensional microtissue assay for high-throughput cytotoxicity of nanoparticles," *Anal Chem.* 84(15):6731-6738, ACS Publications, United States (2012).

Marga, F., et al., Bioprint Engineered Fully Biological Nerve Graft. Poster Presentation TERMIS Dec. 5-8, 2010, Orlando, Florida, 1 page.

Marga, F., et al., "Construction of a Bioprinted Fully Biological Nerve Graft," *Biophysical Journal* 96(3 suppl):643a, Elsevier, Netherlands (Feb. 2009).

Marga, F., et al., "Developmental Biology and Tissue Engineering," *Birth Defects Research (Part C)* 81:320-328, Wiley, United States (2007).

Marga, F., et al., Engineered Fully Biological Nerve Graft. Oral Presentation, International Conference on Biofabrication, Oct. 3-6, 2010, Philadelphia, Pennsylvania, 1 page.

Marga, F., et al., Engineered Fully Biological Nerve Graft. Poster Presentation Biophysical Society Meeting, Mar. 4, 2009, 1 page.

Marga, F., et al., "Toward Engineering Functional Organ Modules by Additive Manufacturing," *Biofabrication* 4:022001, IOP Publishing, United Kingdom (2012).

Martin, I., et al., "Computer-Based Technique for Cell Aggregation Analysis and Cell Aggregation in In Vitro Chondrogenesis," *Cytometry* 28(2):141-146, Wiley, United States (1997).

Mcguigan, A., et al., "Vascularized organoid engineered by modular assembly enables blood perfusion," *PNAS* 103(31):11461-11466, National Academy of Sciences, United States (2006).

Mehesz, A.N., et al., "Scalable robotic biofabrication of tissue spheroids," *Biofabrication* 3:1-8, IOP Publishing, United Kingdom (2011).

Mironov, V., et al., "Bioprinting Living Structures," *J. Mat. Chem.* 17:2054-2060, Royal Society of Chemistry, United Kingdom (2007).

Mironov, V., et al., "Organ Printing: Computer-Aided Jet-Based 3D Tissue Engineering," *Trends in Biotechnology* 21(4):157-161, Elsevier, Netherlands (Apr. 2003).

Mironov, V., et al., "Organ Printing: Self-Assembling Cell Aggregates as 'Bioink'," *Science & Medicine* 9(2):69-71, Elsevier, Netherlands (Apr. 2003).

Mironov, V., et al., "Organ Printing: Tissue Spheroids as Building Blocks," *Biomaterials* 30:2164-2174, Elsevier, Netherlands (2009).

Mizumoto, H., et al., "Formation of Cylindrical Multicellular Aggregate (Cylindroid) and Express of Liver Specific Functions of Primary Rat Hepatocytes," *Cytotechnology* 31:69-75, Springer, Netherlands (1999).

Mombach, J.C., et al., "Quantitative Comparison Between Differential Adhesion Models and Cell Sorting in the Presence and Absence of Fluctuations," *Physical Review Letters* 75(11):2244-2247, American Physical Society, United States (1995).

Moon, S., et al., "Layer by Layer Three-dimensional Tissue Epitaxy by Cell-Laden Hydrogel Droplets," *Tissue Engineering Part C: Methods* 16(1):157-166, Mary Ann Liebert, United States (2010).

Mroue, R., et al., "Three-dimensional cultures of mouse mammary epithelial cells," *Methods Mol Biol.* 945:221-250, Springer Science+Business Media, United States (2013).

Neagu, A., et al., "Role of physical mechanisms in biological self-organization," *Phys Rev Lett* 95(17):178104, American Physical Society, United States (2005).

Newman, S., et al., "Before programs: the physical origination of multicellular forms," *Int J Dev Biol.* 50(2-3):289-299, University of the Basque Country Press, Spain (2006).

Nickerson, C., et al., "Three-Dimensional Tissue Assemblies: Novel Models for the Study of *Salmonella enterica* Serovar Typhimurium Pathogenesis," *Infection and Immunity* 69(11):7106-7120, American Society for Microbiology, United States (Nov. 2001).

Niklason, L.E., et al., "Advances in Tissue Engineering of Blood Vessels and Other Tissues," *Transpl. Immunol.* 5(4):303-306, Elsevier, Netherlands (1997).

Norotte, C., et al., "Scaffold-free vascular tissue engineering using bioprinting," *Biomaterials* 30:5910-5917, Elsevier, Netherlands (2009).

Pathology Outlines: Bladder. Normal Histology. pp. 1-4 (2011).

Paul, S., et al. "How to improve R&D productivity: the pharmaceutical industry's grand challenge," *Nature Reviews Drug Discovery* 9(3):203-214, Springer, Germany (2010).

International Search Report and Written Opinion for International Application No. PCT/US2005/005735, United States Patent Office, United States, dated Dec. 7, 2007, 5 pages.

International Preliminary Report on Patentability for International Application No. PCT/US2005/005735, The International Bureau of WIPO, dated Mar. 3, 2009, 6 pages.

International Search Report for International Application No. PCT/US2009/048530, Korean Intellectual Property Office, Korea, dated Mar. 15, 2010, 4 pages.

International Preliminary Report on Patentability for International Application No. PCT/US2011/023520, The International Bureau of WIPO, dated Aug. 16, 2012, 8 pages.

International Search Report for International Application No. PCT/US2011/023520, Korean Intellectual Property Office, Korea, dated Oct. 31, 2011, 5 pages.

International Preliminary Report on Patentability for International Application No. PCT/US2011/028713, The International Bureau of WIPO, dated Sep. 18, 2012, 5 pages.

International Search Report for International Application No. PCT/US2011/028713, Korean Intellectual Property Office, Korea, dated Nov. 30, 2011, 4 pages.

(56) References Cited

OTHER PUBLICATIONS

International Preliminary Report on Patentability for International Application No. PCT/US2011/053515, The International Bureau of WIPO, dated May 3, 2013, 5 pages.
International Search Report and Written Opinion for International Application No. PCT/US2011/053515, Korean Intellectual Property Office, Korea, dated May 1, 2012, 7 pages.
International Preliminary Report on Patentability for International Application No. PCT/US2012/054923, The International Bureau of WIPO, dated Mar. 20, 2014, 5 pages.
International Search Report for International Application No. PCT/US2012/054923, Korean Intellectual Property Office, Korea, dated Feb. 26, 2013, 4 pages.
International Preliminary Report on Patentability for International Application No. PCT/US2012/054935, The International Bureau of WIPO, dated Mar. 20, 2014, 7 pages.
International Search Report for International Application No. PCT/US2012/054935, Korean Intellectual Property Office, Korea, dated Feb. 28, 2013, 4 pages.
International Preliminary Report on Patentability for International Application No. PCT/US2013/036479, The International Bureau of WIPO, dated Oct. 21, 2014, 8 pages.
International Search Report for International Application No. PCT/US2013/036479, Korean Intellectual Property Office, Korea, dated Jul. 25, 2013, 4 pages.
International Preliminary Report on Patentability for International Application No. PCT/US2013/046519, The International Bureau of WIPO, dated Dec. 23, 2014, 11 pages.
International Search Report for International Application No. PCT/US2013/046519, Korean Intellectual Property Office, Korea, dated Sep. 5, 2013, 3 pages.
International Preliminary Report on Patentability for International Application No. PCT/US2014/026679, The International Bureau of WIPO, dated Sep. 24, 2015, 10 pages.
International Search Report and Written Opinion for International Application No. PCT/US2014/026679, Korean Intellectual Property Office, Korea, dated Jul. 22, 2014, 12 pages.
International Search Report and Written Opinion for International Application No. PCT/US2014/041419, Korean Intellectual Property Office, Korea, dated Jan. 2, 2015, 35 pages.
International Search Report and Written Opinion for International Application No. PCT/US2014/048962, Korean Intellectual Property Office, Korea, dated Nov. 10, 2014, 7 pages.
Perez-Pomares, J., et al., "Tissue Fusion and Cell Sorting in Embryonic Development and Disease: Biomedical Implications," *Bioessays* 28:809-821, Wiley, United States (2006).
Remuzzi, A., et al., "Vascular Smooth Muscle Cells on Hyaluronic Acid: Culture and Mechanical Characterization of an Engineered Vascular Construct," *Tissue Engineering* 10(516):699-710, Mary Ann Liebert, United States (2004).
Riken. Self-healing hydrogels ease into production. Research Highlights: Materials. Downloaded from the Riken website: <http://www.riken.jp/en/research/rikenresearch/highlights/7543/> (Nov. 1, 2013) [accessed Apr. 27, 2015].
Ryan, P.L., et al., "Tissue Spreading on Implantable Substrates is a Competitive Outcome of Cell-Cell vs. Cell-Substratum Adhesivity," *PNAS* 98(8):4323-4327, National Academy of Sciences, United States (2001).
Schuster, D., et al., "Why Drugs Fail—A Study on Side Effects in New Chemical Entities," *Curr. Pharm. Des.* 11:3545-3559, Bentham Science Publishers, United Arab Emirates (2005).
Shafrir, Y., et al., "Mechanotransduction through the cytoskeleton," *American Journal of Physiology* 282:479-486, American Physiological Society, United States (2002).
Sheehan, T., et al., "Recent Patents and Trends in Bioprinting," *Recent Patents on Biomedical Engineering* 4:26-32, Bentham Science Publishers, United Arab Emirates (2011).
Shim, J., et al., "Bioprinting of a mechanically enhanced three-dimensional dual cell-laden construct for osteochondral tissue engineering using a multi-head tissue/organ building system," *J of Micromechanics and Microengineering.* 22:1-11, IOP Publishing, United Kingdom (2012).
Siemionow, M., et al. "Current Techniques and Concepts in Peripheral Nerve Repair. Chapter 8," *International Review of Neurobiology* 87:141-172, Academic Press, United States (2009).
Skardal, A., et al., "Bioprinting vessel-like constructs using hyaluronan hydrogels crosslinked with tetrahedral polyethylene glycol tetracrylates," *Biomaterials* 31:6173-6181, Elsevier, Netherlands (2010).
Smith. A direct-write three-dimensional Bioassembly tool for regenerative medicine. The University of Arizona pp. 1-291 (Nov. 1, 2005).
Smith, C., et al. "Characterizing Environment Factors that Impact the Viability of Tissue-Engineered Constructs Fabricated by a Direct-Write Bioassembly Tool," *Tissue Engineering* 13(2):373-385, Mary Ann Liebrt, United States (2007).
Smith, C., et al., "Three-Dimensional BioAssembly Tool for Generating Viable Tissue-Engineered Constructs," *Tissue Engineering* 10(9/10):1566-1576, Mary Ann Liebert, United States (2004).
Steinberg, M.S., "Does Differential Adhesion Govern Self-Assembly Processes in Histogenesis? Equilibrium Configurations and the Emergence of a Hierarchy Among Populations of Embryonic Cells," *The Journal of Experimental Zoology* 173(4):395-433, Wiley, United States (Apr. 1970).
Steinberg, M., et al. Liquid Behavior of Embryonic Tissues. Cell Behaviour pp. 583-697 (1982).
Stiles. UA Wins R & D 100 Award for Machine that Prints Tissue Cell-by-Cell. UANews Dec. 2, 2003, http://uanews.org/cgi-binffleb0bjects/UANews.woa/wa/goPrint?ArticleID=8305, accessed on Feb. 1, 2005, 2 pages.
Tang, M., et al., "Molding of Three-Dimensional Microstructures of Gels," *Journal of the American Chemical Society* 125(43):12988-12989, American Chemical Society, United States (2003).
Tao et al. Bio-printing of living organized tissues using an inkjet technology. Database Accession No. PREV200700335042. FASEB Journal 23(5):A636 (2007).
Timmins, N., et al., "Hanging-Drop Multicellular Spheroids as a Model of Tumour Angiogenesis," *Angiogenesis* 7(2):97-103, Springer, Netherlands (2004).
Tsang, V., and Bhatia, S., "Three-Dimensional Tissue Fabrication," *Advanced drug delivery Reviews* 56(11):1635-1647, Elsevier, Netherlands (2004).
Office action dated Jan. 6, 2011, in U.S. Appl. No. 10/590,446, Forgacs, G., et al., filed Oct. 10, 2007, 13 pages.
Office action dated Sep. 1, 2011, in U.S. Appl. No. 10/590,446, Forgacs, G., et al., filed Oct. 10, 2007, 14 pages.
Office action dated Oct. 28, 2004, in U.S. Appl. No. 10/666,836, Boland, T., et al., filed Sep. 17, 2003, 5 pages.
Office action dated Dec. 10, 2008, in U.S. Appl. No. 11/227,489, Robbins, N., et al., filed Sep. 16, 2005, 16 pages.
Office action dated Jul. 8, 2009, in U.S. Appl. No. 11/227,489, Robbins, N., et al., filed Sep. 16, 2005, 11 pages.
Office action dated Dec. 31, 2012, in U.S. Appl. No. 13/020,000, Forgacs, G., et al., filed Feb. 2, 2011, 15 pages.
Office action dated Jul. 3, 2013, in U.S. Appl. No. 13/020,000, Forgacs, G., et al., filed Feb. 2, 2011, 15 pages.
Office Action dated Aug. 26, 2014, U.S. Appl. No. 13/246,428, Murphy, K., et al., filed Sep. 27, 2011, 9 pages.
Office Action dated Jan. 14, 2015, in U.S. Appl. No. 13/246,428, Murphy, K., et al., filed Sep. 27, 2011, 10 pages.
Office Action dated Mar. 19, 2013, in U.S. Appl. No. 13/402,215, Forgacs, G., et al., filed Feb. 22, 2012, 15 pages.
Office action dated Sep. 24, 2013, in U.S. Appl. No. 13/529,172, Forgacs, G., et al., filed Jun. 21, 2012, 13 pages.
Office Action dated Jul. 30, 2015, in U.S. Appl. No. 13/612,768, Murphy, K., et al., filed Sep. 12, 2012, 13 pages.
Office Action dated May 30, 2014, in U.S. Appl. No. 13/612,768, Murphy, K., et al., filed Sep. 12, 2012, 16 pages.
Office Action dated Nov. 17, 2014, in U.S. Appl. No. 13/612,768, Murphy, K., et al., filed Sep. 12, 2012, 28 pages.
Office Action dated Oct. 1, 2013, in U.S. Appl. No. 13/612,768, Murphy, K., et al., filed Sep. 12, 2012, 13 pages.

(56) References Cited

OTHER PUBLICATIONS

Office Action dated Apr. 28, 2014, in U.S. Appl. No. 13/612,778, Murphy, K., et al., filed Sep. 12, 2012, 20 pages.
Office Action dated Nov. 7, 2014, in U.S. Appl. No. 13/612,778, Murphy, K., et al., filed Sep. 12, 2012, 18 pages.
Office Action dated Jan. 28, 2015, in U.S. Appl. No. 13/634,863, Khatiwala, C., et al., filed May 15, 2013, 7 pages.
Office Action madated iled Sep. 8, 2015, in U.S. Appl. No. 13/634,863, Khatiwala, C., et al., filed May 15, 2013, 9 pages.
Office Action dated May 8, 2015, in U.S. Appl. No. 13/794,368, Murphy, K., et al., filed Mar. 11, 2013, 21 pages.
Office Action dated Nov. 26, 2014, in U.S. Appl. No. 13/794,368, Murphy, K., et al., filed Mar. 11, 2013, 16 pages.
Office Action dated Sep. 23, 2015, in U.S. Appl. No. 13/794,368, Murphy, K., et al., filed Mar. 11, 2013, 18 pages.
Office Action dated Jun. 5, 2015, in U.S. Appl. No. 13/801,780, Presnell, S., et al., filed Mar. 13, 2013, 18 pages.
Office Action dated Nov. 14, 2014, in U.S. Appl. No. 13/801,780, Presnell, S., et al., filed Mar. 13, 2013, 20 pages.
Office Action dated Jun. 26, 2014, in U.S. Appl. No. 13/968,313, Murphy, K., et al., filed Aug. 15, 2013, 10 pages.
Office Action dated Oct. 23, 2015, in U.S. Appl. No. 14/244,679, Forgacs, G., et al., filed Apr. 3, 2014, 16 pages.
Office Action dated May 7, 2015, in U.S. Appl. No. 14/295,226, Shepherd, B., et al., filed Jun. 3, 2014, 17 pages.
Office Action dated Oct. 8, 2014, in U.S. Appl. No. 14/295,226, Shepherd, B., et al., filed Jun. 3, 2014, 10 pages.
Office Action dated Sep. 9, 2015, in U.S. Appl. No. 14/295,226, Shepherd, B., et al., filed Jun. 3, 2014, 9 pages.
Office Action dated Jul. 15, 2015, in U.S. Appl. No. 14/447,412, Murphy, K., et al., filed Jul. 30, 2014, 13 pages.
Office Action dated Mar. 3, 2015, in U.S. Appl. No. 14/447,412, Murphy, K., et al., filed Jul. 30, 2014, 36 pages.
Office Action dated May 14, 2015, in U.S. Appl. No. 14/530,499, Murphy, K., et al., filed Oct. 31, 2014, 6 pages.
Office Action dated Oct. 8, 2015, in U.S. Appl. No. 14/678,392, King, S., et al., filed Apr. 3, 2015, 25 pages.
Office Action dated Sep. 24, 2015, in U.S. Appl. No. 14/678,392, King, S., et al., filed Apr. 3, 2015, 26 pages.
Office Action dated Sep. 25, 2015, in U.S. Appl. No. 14/796,910, Murphy, K., et al., filed Jul. 10, 2015, 9 pages.
Wake Forest Baptist Medical Center (Wake Forest Physician Reports First Human Recipients of Laboratory-Grown Organs. 2006 pp. 1-2).
Wang, J., et al., "Bone marrow mesenchymal stem cells promote cell proliferation and neurotrophic function of Schwann cells in vitro and in vivo," *Brain Research* 1262:7-15, Elsevier, Netherlands (2009).
Xu, F., et al., "A three-dimensional in vitro ovarian cancer coculture model using a high-throughput cell patterning platform," *Biotechnology Journal* 6(2):204-212, Wiley, United States (2011).
Xu, F., et al., "In vivo generation of functional tissues using the inkjet printing technology," *Tissue Engineering*, 13(7):1713-1714, Mary Ann Liebert, United States (2007).
Yamauchi, N., et al., "A Three-Dimensional Cell Culture Model for Bovine Endometrium: Regeneration of a Multicellular Spheroid Using Ascorbate," *Placenta* 24:258-269, Elsevier, Netherlands (2003).
Zhang, Y., et al., "Characterization of printable cellular microfluidic channels for tissue engineering," *Biofabrication* 5:025004, IOP Publishing, United Kingdom (2013).
Fujita, H., et al., "Fabrication of scaffold-free contractile skeletal muscle tissue using magnetite-incorporated myogenic C2C12 cells," *J Tissue Eng Regen Med* 4(6):437-443, Wiley, United States (2010).
Hierlihy, A., et al., "The post-natal heart contains a myocardial stem cell population," *FEBS Letters* 530:239-243, Wiley, United States (2002).
Liu, C., et al., "Design and Development of Three-Dimensional Scaffolds for Tissue Engineering," *Chemical Engineering Research and Design* 85(7):1051-1064, Elsevier, Netherlands (2007).
Pearson Education. Human Heart Illustration (2004).
Tanaka, K., et al., "A valved hepatic portoduodenal intestinal conduit for billary atresia," *Ann Surg.* 213(3):230-235, Lippincott Williams & Wilkins, United States (1991).
Tsang, V., et al., "Fabrication of 3D hepatic tissues by additive phtopatterning of cellular hydrogels," *The FASEB Journal* 21(3):790-801, Federation of American Societies for Experimental Biology, United States (2007).
Office Action dated Nov. 17, 2015, in U.S. Appl. No. 13/612,778, Murphy, K., et al., filed Sep. 12, 2012, 25 pages.
Office action dated May 29, 2020, in U.S. Appl. No. 15/765,110, Retting, K., et al., filed Mar. 30, 2018, 15 pages.
Office action dated Apr. 1, 2021, in U.S. Appl. No. 15/765,110, Retting, K., et al., filed Mar. 30, 2018, 16 pages.

Fig. 5
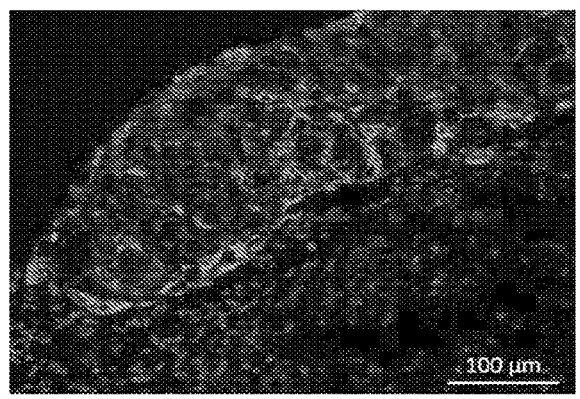
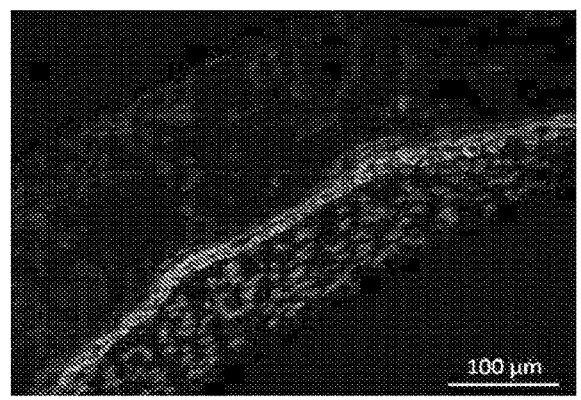
A　　　　　　　　　　　B

Fig. 11
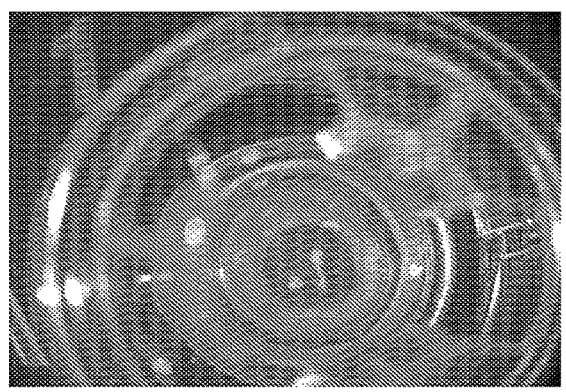
A
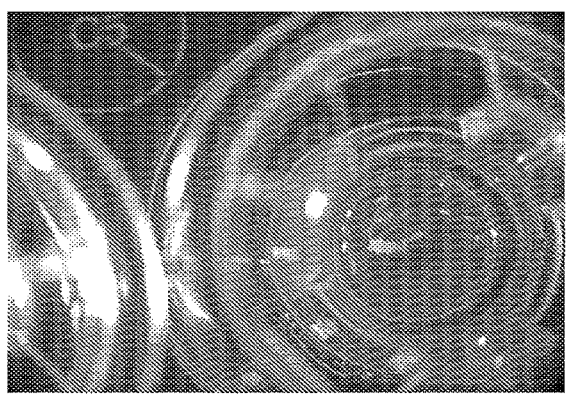
B
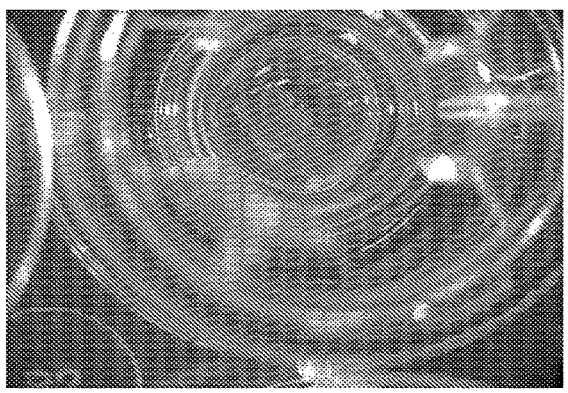
C
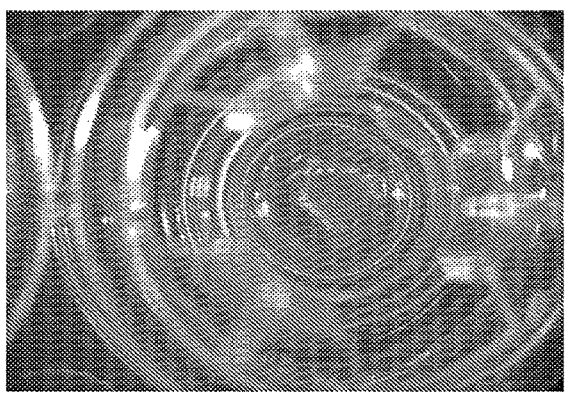
D

Fig. 12
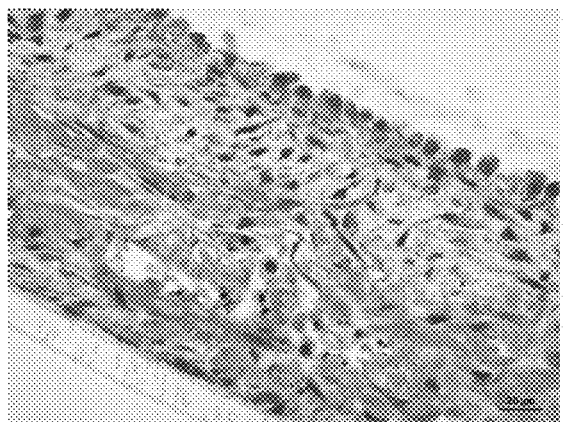 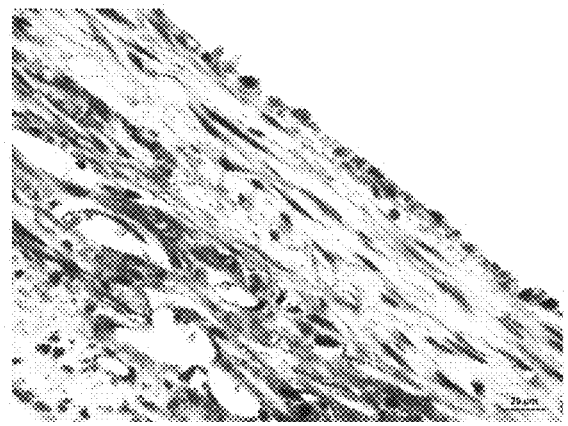
A  B

Fig. 13
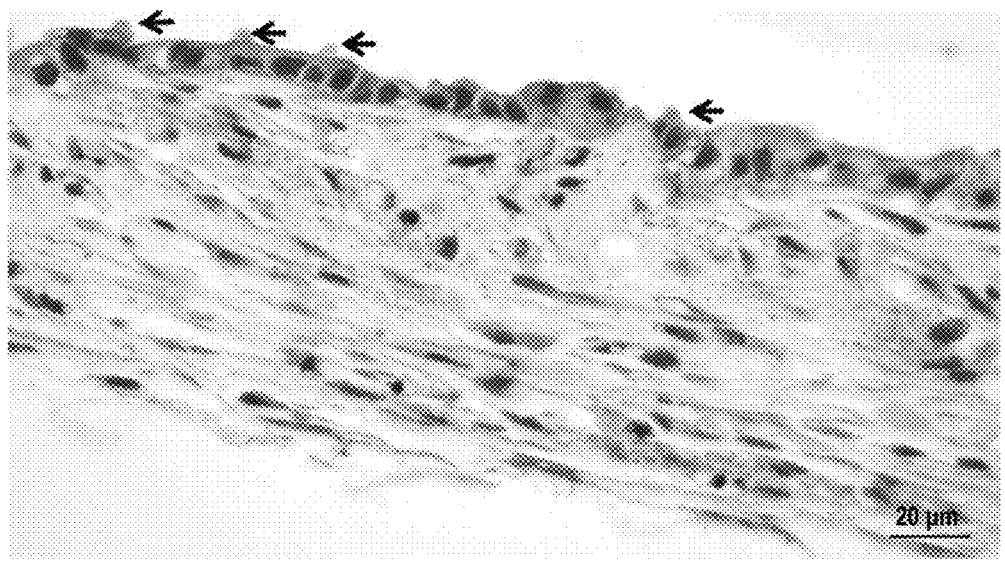
A
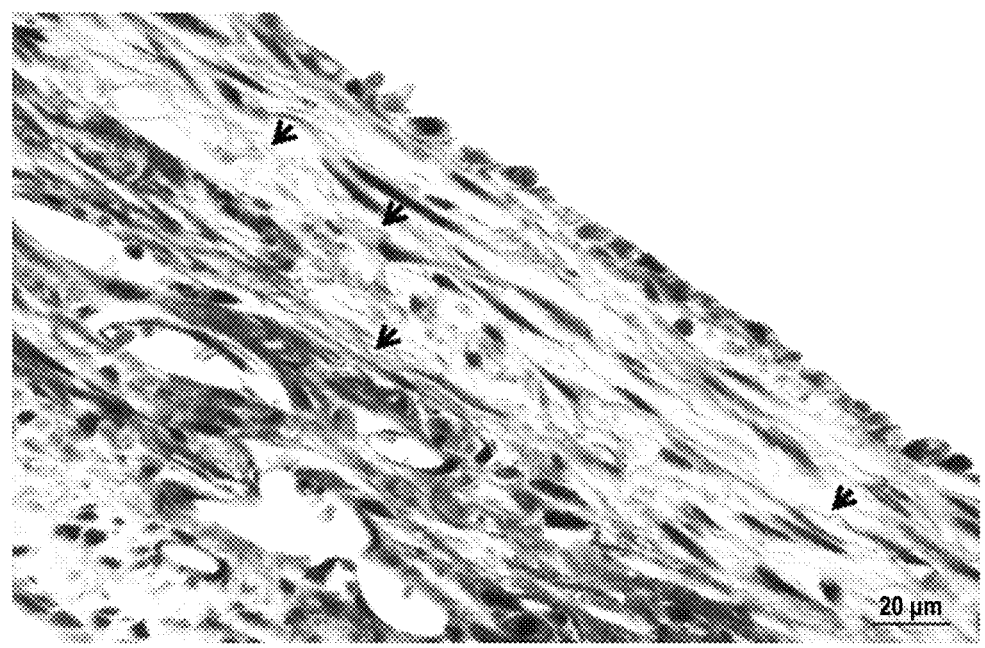
B

METHODS FOR TISSUE FABRICATION

BACKGROUND OF THE INVENTION

Tissue engineering and regenerative medicine is a field with great promise from both a therapeutic and a research standpoint. Engineered tissues are at the center of many different avenues of tissue engineering research. Methods that can improve the fabrication and formation of these tissues, can also improve their function both in vitro and in vivo, and are needed in order to facilitate the advancement of this field.

SUMMARY OF THE INVENTION

While tissue engineering holds great potential for mankind, many problems must be overcome before the full extent of these advantages can be realized. One of the problems in tissue engineering is achieving and maintaining compartmentalization of cell types within a tissue. While bioprinting overcomes some of those challenges in the initial fabrication step, new methods are needed that are broadly applicable and support achievement and maintenance of cellular compartments post fabrication without compromising cell viability and function. For example, one way to induce compartmentalization is to utilize calcium-cross-linked hydrogels as a component of bio-ink. Disadvantages of this method are that very high concentrations of divalent cross-linking compounds such as calcium ions can negatively impact viability in the tissue, and removal of the hydrogel components requires treatment with enzymes or chemicals that may further damage the cells. Therefore, a method of compartmentalized tissue fabrication has been developed that can be applied broadly and maintains cellular compartments and avoids ionic cross-linkers and enzymatic hydrogel removal post-fabrication. In certain aspects, this disclosure allows for the fabrication of engineered tissues without the necessity of cross-linking for tissue formation.

Disclosed herein are methods that improve the viability of bioprinted tissues, and more quickly facilitate formation of tissue geometries, improve tissue uniformity and enhance and maintain compartmentalization post fabrication as required for the tissues to be used in research and therapeutic applications. These methods consist of a "hypothermic hold" or exposure after bioprinting, followed by a maturation or incubation at a temperature below 37° C. This allows for elimination of a cross-linking step improving subsequent tissue morphology, cell viability, and differentiation as assayed by gene expression as shown in FIGS. 11, 16, and 17 respectively.

Described herein is a method of fabricating a three-dimensional, engineered, biological tissue, the method comprising: preparing a bio-ink comprising living cells; depositing the bio-ink onto a surface by extrusion bioprinting; incubating the bio-ink at a temperature of greater than or equal to 18° C., but less than 37° C.; wherein the bio-ink is not exposed to any ionic, chemical, photo or physical cross-linker during the incubation at a temperature of greater than or equal to 18° C., but less than 37° C. In certain embodiments, apoptosis in a bioprinted tissue is reduced by fabrication using said method, in comparison to an engineered tissue not fabricated by said method. In certain embodiments, the method further comprises exposing the bio-ink to a hypothermic hold of greater than or equal to 2° C., but less than 10° C. during or after bioprinting. In certain embodiments, the bio-ink is not exposed to any ionic, chemical, photo or physical cross-linker during the hypothermic hold of greater than or equal to 2° C., but less than 10° C. during or after bioprinting. In certain embodiments, apoptosis in a bioprinted tissue is reduced by fabrication using said method, in comparison to an engineered tissue not fabricated by said method. In certain embodiments, the bio-ink further comprises a test substance, the test substance a substance under evaluation for its ability to elicit a change in a tissue compared to a tissue not treated with said substance. In certain embodiments, the bio-ink is not deposited by aerosol spray technology. In certain embodiments, the bio-ink consists essentially of a single human cell-type.

Also described herein is a method of fabricating a three-dimensional, engineered, biological tissue, the method comprising: preparing a plurality of bio-inks comprising living cells; depositing a first bio-ink onto a surface by extrusion bioprinting; incubating the first bio-ink at a temperature of greater than or equal to 18° C., but less than 37° C.; depositing a second bio-ink onto a surface by extrusion bioprinting; and incubating the plurality of bio-inks at a temperature of greater than or equal to 18° C., but less than 37° C.; wherein the bio-ink is not exposed to any ionic, chemical, photo or physical cross-linker during the exposure of the first bio-ink, the second bio ink, or both bio-inks at a temperature of greater than or equal to 18° C., but less than 37° C. In certain embodiments, apoptosis in a bioprinted tissue is reduced by fabrication using said method, in comparison to an engineered tissue not fabricated by said method. In certain embodiments the method further comprises exposing the first bio-ink, the second bio-ink, or both bio-inks to a temperature of greater than or equal to 2° C., but less than 10° C. during or after bioprinting. In certain embodiments, the bio-ink is not exposed to any ionic, chemical, photo or physical cross-linker during the hypothermic hold of greater than or equal to 2° C., but less than 10° C. during or after bioprinting. In certain embodiments, apoptosis in a bioprinted tissue is reduced by fabrication using said method, in comparison to an engineered tissue not fabricated by said method. In certain embodiments, at least one of the first or second bio-inks or both bio-inks comprise a test substance, wherein the test substance is a substance under evaluation for its ability to elicit a change in a tissue compared to a tissue not treated with said substance. In certain embodiments, the first or second bio-ink is not deposited by aerosol spray technology.

Also described herein is a three-dimensional, engineered, biological tissue, the tissue engineered by: preparing a bio-ink comprising living cells; depositing the bio-ink onto a surface by extrusion bioprinting; incubating the bio-ink at a temperature of greater than or equal to 18° C., but less than 37° C.; not exposing the tissue to any ionic, chemical, photo or physical cross-linker during the incubation at a temperature of greater than or equal to 18° C., but less than 37° C.; and wherein the tissue exhibits lower levels of apoptosis than a tissue that has been incubated at 37° C. or above. In certain embodiments, the bio-ink is exposed to a temperature of greater than or equal to 2° C., but less than 10° C. during or after bioprinting. In certain embodiments, the bio-ink was not exposed to any ionic, chemical, photo or physical cross-linker during the hypothermic hold of greater than or equal to 2° C., but less than 10° C. during or after bioprinting. In certain embodiments, the bio-ink further comprises a test substance, wherein a test substance is a substance under evaluation for its ability to elicit a change in a tissue compared to a tissue not treated with said substance. In certain embodiments, the bio-ink was not deposited by aerosol spray technology. In certain embodiments, the bio-ink consists essentially of a single human cell type. In certain embodiments, the tissue has no perfusable vasculature. In certain embodiments, the tissue consists essentially of a single human cell-type.

Also described herein is a three-dimensional, engineered, biological tissue, the tissue engineered by: preparing a plurality of bio-inks comprising living cells; depositing a first bio-ink onto a surface by extrusion bioprinting; incubating the first bio-ink at a temperature of greater than or equal to 18° C., but less than 37° C.; depositing a second bio-ink onto a surface by extrusion bioprinting; incubating the plurality of bio-inks at a temperature of greater than or equal to 18° C., but less than 37° C.; and not exposing any bio-ink to any ionic, chemical, photo or physical cross-linker during the exposure of the first bio-ink, the second bio ink, or both bio-inks at a temperature of greater than or equal to 18° C., but less than 37° C.; wherein the tissue exhibits lower levels of apoptosis than a tissue that has been incubated at 37° C. or above. In certain embodiments, the bio-ink was exposed to a temperature of greater than or equal to 2° C., but less than 10° C. during or after bioprinting. In certain embodiments, the bio-ink was not exposed to any ionic, chemical, photo or physical cross-linker during the hypothermic hold of greater than or equal to 2° C., but less than 10° C. during or after bioprinting. In certain embodiments, at least one of the plurality of bio-inks further comprises a test substance, wherein a test substance is a substance under evaluation for its ability to elicit a change in a tissue compared to a tissue not treated with said substance. In certain embodiments, the first or second bio-ink was not deposited by aerosol spray technology. In certain embodiments, the tissue has no perfusable vasculature. In certain embodiments, any of the first or second bio-inks consist essentially of a single human cell-type.

In yet another aspect, disclosed herein are three-dimensional, engineered biological tissues comprising: a bio-ink, wherein the bio-ink comprises a concentration of between 0.1 and 50 million cells per mL, and a concentration of NOVOGEL between 2 and 20%, wherein the bio-ink is held at a temperature of between 2-10° C. for between 30 seconds and 1 hour.

In yet another aspect, disclosed herein are three-dimensional, engineered biological tissues comprising: a bio-ink, wherein the bio-ink comprises a concentration of between 0.1 and 50 million cells per mL, and a concentration of NOVOGEL between 2 and 20%, wherein the bio-ink is held at a temperature of between 18-37° C. for between 1 hour and 15 days.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5 shows non-limiting examples of photomicrographs of engineered skin tissues of Example 1; in this case, photomicrographs depicting a comparison of tissues bioprinted using different methodologies (first tissue at day 10 (A); second tissue at day 12 (B)).

FIG. 11 shows a macroscopic view comparing cells bioprinted as per Example 3 at either 37° C. (A and B) or 30° C. (C and D).

FIG. 12 shows H&E (A) and trichrome (B) staining of bioprinted renal tissue constructs from Example 3.

FIG. 13 shows the constructs from FIG. 11 with brush borders (A, arrows), and collagen deposition (B, arrows) highlighted.

DETAILED DESCRIPTION OF THE INVENTION

In one aspect, disclosed herein are methods of fabricating a three-dimensional, engineered, biological tissue, the method comprising, preparing a bio-ink comprising living cells; depositing the bio-ink onto a surface by bioprinting; incubating the bio-ink at a temperature of greater than or equal to 18° C., but less than 37° C.; wherein the bio-ink is not exposed to any ionic, chemical, photo or physical cross-linker during the incubation at a temperature of greater than or equal to 18° C., but less than 37° C.

In another aspect, disclosed herein are methods of fabricating a three-dimensional, engineered, biological tissue, the method comprising: preparing a plurality of bio-inks comprising living cells; depositing a first bio-ink onto a surface by bioprinting; incubating the first bio-ink at a temperature of greater than or equal to 18° C., but less than 37° C.; depositing a second bio-ink onto the surface by bioprinting; and incubating the plurality of bio-inks at a temperature of greater than or equal to 18° C., but less than 37° C.; and wherein the bio-ink is not exposed to any ionic, chemical, photo or physical cross-linker during the exposure of the first bio-ink, the second bioink, or both bio-inks at a temperature of greater than or equal to 18° C., but less than 37° C.

In another aspect, disclosed herein are three-dimensional, engineered, biological tissues, the tissues engineered by: preparing a bio-ink comprising living cells; depositing the bio-ink onto a surface by bioprinting; incubating the bio-ink at a temperature of greater than or equal to 18° C., but less than 37° C.; wherein the bio-ink is not exposed to any ionic, chemical, photo or physical cross-linker during the incubation at a temperature of greater than or equal to 18° C., but less than 37° C.

In another aspect, disclosed herein are three-dimensional, engineered, biological tissues, the tissues engineered by: preparing a plurality of bio-inks comprising living cells; depositing a first bio-ink onto a surface by bioprinting; incubating the first bio-ink at a temperature of greater than or equal to 18° C., but less than 37° C.; depositing a second bio-ink onto the surface by bioprinting; and incubating the plurality of bio-inks at a temperature of greater than or equal to 18° C., but less than 37° C.; and wherein the bio-ink is not exposed to any ionic, chemical, photo or physical cross-linker during the exposure of the first bio-ink, the second bioink, or both bio-inks at a temperature of greater than or equal to 18° C., but less than 37° C.

Figure 16:
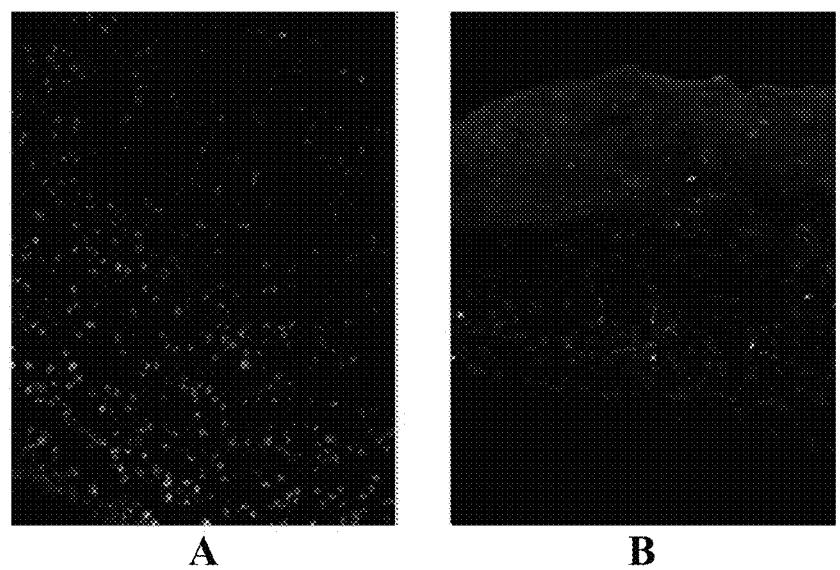
FIG. 16 shows an example of skin tissue printed using the methods of this disclosure a 4° C. hypothermic hold for 10 minutes, followed by a 30° C. incubation for 5 days at no point was the tissue construct exposed to a cross-linking step, TUNEL staining (green) indicates lower levels of apoptosis (B) when compared to a tissue printed not using these techniques (A).

An advantage of the engineered tissues and methodologies described herein is that they allow retention of the shape of the structure without compromising the functionality of the original cell types, and that they require no use of potentially toxic cross-linkers such as high ion levels, enzymes or UV light. The shape of the bioprinted structure is advantageously maintained by multiple approaches. A cold exposure step and/or an incubation step at below 37° C. are advantageous in that they allow for printed bio-inks to better maintain their shape during maturation, and limit the bioprinted cells exposure to cross-linkers that may damage the cells, such as supraphysiological levels of calcium, and reduces apoptosis in the resulting bioprinted tissues (FIG. 16). Surprisingly, this works with multiple tissue types, and even tissue types that are normally internal to the body, and, thus, at 37° C. (FIG. 11, kidney tissue). A temporal delay between printing bio-inks allows for maturation of a basal layer before application of any succeeding layer. The invention also incorporates a novel aerosol spray printing method into a 3D tissue model. The aerosol spray approach provides a for a unique discontinuous method compared to a continuous deposition method in that it allows the creation of a thinner layer, and allows for deposition of material onto an existing tissue layer after a period of maturation. This is advantageous because it may produce a tissue that better mimics native tissue in vivo. This can also be advantageous because it can reduce the number of cells required and allow for bioprinting with limited cell populations. This aerosol spray method can be applied to create multiple layers at multiple time points. For example, this method could be used for constructing a skin tissue by spraying first with undifferentiated keratinocytes followed by spraying with differentiated keratinocytes this could better mimic native skin.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As used herein, "consists essentially" means that the specified cell type is the only cell type present, but the bio-ink may contain other non-cellular material including but not limited to extrusion compounds, hydrogels, extracellular matrix components, nutritive and media components, inorganic and organic salts, acids and bases, buffer compounds, and other non-cellular components that promote cell survival, adhesion, growth, or that facilitate bioprinting.

As used herein "exposed" to a "cross-linker" or "cross-linking" agent means non-physiological levels of the specific cross-linker or cross-linking agent, or levels of the specific cross-linking agent that are not sufficient to result in significant crosslinking of a given cross-linkable substance. Significant crosslinking is greater than 1%, 2%, 3%, 4% or 5% crosslinking.

As used herein, "tissue" means an aggregate of cells.

As used herein, "layer" means an association of cells in X and Y planes that is multiple cells thick. In some embodiments, the engineered tissues describe herein include one layer. In other embodiments, the engineered tissues describe herein include a plurality of layers. In various embodiments, a layer forms a contiguous, substantially contiguous, or non-contiguous sheet of cells. In some embodiments, each layer of an engineered tissue described herein comprises multiple cells in the X, Y, and Z axes.

As used herein, "bio-ink" means a liquid, semi-solid, or solid composition for use in bioprinting. In some embodiments, bio-ink comprises cell solutions, cell aggregates, cell-comprising gels, multicellular bodies, cellular pastes or tissues. In some embodiments, the bio-ink additionally comprises non-cellular materials that provide specific biomechanical properties that enable bioprinting. In some embodiments, the bio-ink comprises an extrusion compound. In some cases, the extrusion compound is engineered to be removed after the bioprinting process. In other embodiments, at least some portion of the extrusion compound remains entrained with the cells post-printing and is not removed.

As used herein, "bio-compatible liquid" means any liquid capable of contacting or completely covering cells without damage to the cells, examples include but are not limited to growth media and physiological buffers disclosed in this application.

As used herein, "bioprinting" means utilizing three-dimensional, precise deposition of cells (e.g., cell solutions, cell-containing gels, cell suspensions, cell concentrations, multicellular aggregates, multicellular bodies, etc.) via methodology that is compatible with an automated or semi-automated, computer-aided, three-dimensional prototyping device (e.g., a bioprinter). Suitable bioprinters include the NOVOGEN BIOPRINTER from Organovo, Inc. (San Diego, CA). Some bioprinting methods are extrusion methods which comprise forcing a high viscosity bio-ink through an opening for deposition to a surface. Extrusion methods can be continuous or discontinuous. Other bioprinting methods are ejection methods which comprise spraying an aerosol, droplets, or a mist onto a surface. This type of method requires a low-viscosity bio-ink. An example of this method is the technique of ink-jetting. These methods are incompatible with high viscosity bio-inks.

As used herein, "scaffold" refers to synthetic scaffolds such as polymer scaffolds and porous hydrogels, non-synthetic scaffolds such as pre-formed extracellular matrix layers, dead cell layers, and decellularized tissues, and any other type of pre-formed scaffold that is integral to the physical structure of the engineered tissue and not able to be removed from the tissue without damage/destruction of said tissue. In further embodiments, decellularized tissue scaffolds include decellularized native tissues or decellularized cellular material generated by cultured cells in any manner; for example, cell layers that are allowed to die or are decellularized, leaving behind the ECM they produced while living. The term "scaffoldless," therefore, is intended to imply that pre-formed scaffold is not an integral part of the engineered tissue at the time of use, either having been removed or remaining as an inert component of the engineered tissue. "Scaffoldless" is used interchangeably with "scaffold-free" and "free of pre-formed scaffold."

As used herein, "subject" means any individual, which is a human, a non-human animal, any mammal, or any vertebrate. The term is interchangeable with "patient," "recipient" and "donor."

As used herein, "test substance" refers to any biological, chemical or physical substance under evaluation for its ability to elicit a change in said skin tissue compared to skin tissue not treated with said substance. A non-limiting example of a change in skin tissue could be an allergic reaction, a toxic reaction, an irritation reaction; a change that is measured by a defined molecular state such as a change in mRNA levels or activity, changes in protein levels, changes in protein modification or epigenetic changes; or a change that results in a measurable cellular outcome such as a change in proliferation, apoptosis, cell viability, cell division, cell motility, cytoskeletal rearrangements, chromosomal number or composition. Test substances include, but are not limited to; chemical compositions containing an active or inactive ingredient, either in whole, in part, isolated, or purified; physical stressors such as light, UV light, mechanical stress, heat, or cold; biological agents such as bacteria, viruses, parasites, or fungi. "Test substance" also refers to a plurality of substances mixed or applied separately.

As used herein, "use" encompasses a variety of possible uses of the tissue which will be appreciated by one skilled in the art. These uses include by way of non-limiting example; implantation or engraftment of the engineered tissue into or onto a subject; inclusion of the tissue in a biological assay for the purposes of biological, biotechnological or pharmacological discovery; toxicology testing, including teratogen testing; pharmacology testing, including testing to determine pharmacokinetics and drug metabolism and absorption and penetration, cosmetic testing, including testing to determine sensitization, potential to cause irritation or corrosion of any layer of the dermis, to any test chemical or non-chemical agent including ultraviolet light. "Use" can also refer to the process of maturation, or tissue cohesion, in vitro after bioprinting.

Engineered, Three-Dimensional Tissues

One advantage to fabricating tissue with the bioprinting platform disclosed herein compared to current tissue models and natural tissue is that the process is automated. This allows for greater reproducibility and scalability. For example, it is possible to miniaturize the tissue geometry in order to print bio-ink into well plate formats such as 6, 12, 24, 48, 96, 384 or 1536-well plates for use in screening applications including high-throughput screening applications. Another major advantage of an automated platform is that it can be utilized to administer substances for toxicity testing in addition to bioprinting tissue. Current testing in tissue models is limited by the manual approaches necessary both to fabricate the tissue and to apply a test material to that tissue, limiting the application to topical administration. The flexibility of the printing platform allows for a variety of methods for application, deposition, and incorporation into tissues not possible with a manual approach. For example, test substances could be sprayed in a fine mist using the aerosol spray technology, or injected into the dermal layer utilizing the continuous deposition module. A third major advantage of bioprinting in a tissue toxicology model is the time frame in which a layered structure can be generated and tested. Bioprinting approaches can overlay sheets of cells simultaneously or with a delay to create multiple layers which can then be allowed to mature and differentiate for a defined period of time. The bioprinting platform allows for longitudinal studies not possible with manual approaches because test or therapeutic substances can be exposed to or incorporated into tissues during printing or administered to mature tissues at later time points.

In some embodiments, the three-dimensional, engineered, biological tissues described herein include one or more cellular layers. In further embodiments, the layers are stratified. In some embodiments, the engineered tissues include a basal layer. In some embodiments, the tissues described herein are skin tissues. In some embodiments, the tissues described herein are kidney tissues. In some embodiments, the tissues described herein are liver tissues. In some embodiments, the tissues described herein are lung tissues. In some embodiments, the tissues described herein are gut tissues. In some embodiments, the tissues described herein are intestinal tissues.

In some embodiments, the cells are bioprinted. In further embodiments, the bioprinted cells are cohered to form the engineered tissues. In still further embodiments, the engineered tissues are free or substantially free of pre-formed scaffold at the time of fabrication or the time of use. In some cases, bioprinting allows fabrication of tissues that mimic the appropriate cellularity of native tissue.

In some embodiments, the three-dimensional, engineered tissues described herein are distinguished from tissues fabricated by prior technologies by virtue of the fact that they are three-dimensional, free of pre-formed scaffolds, consist essentially of cells, have a high cell density. In certain embodiments, the engineered tissues are greater than 30% cellular, greater than 40% cellular, greater than 50% cellular, greater than 60% cellular, greater than 70% cellular, greater than 80% cellular, or greater than 90% cellular. In certain embodiments, the engineered tissues have been exposed to incubations at different non-physiological temperatures at various times. For mammalian cells physiological temperature is defined as the normal body temperature of about 37° C.

Distinguished from Native Tissue

In some embodiments, the three-dimensional, engineered tissues described herein are distinguished from native (e.g., non-engineered) tissues by virtue of the fact that they are non-innervated (e.g., substantially free of nervous tissue), substantially free of mature vasculature, and/or substantially free of blood components. For example, in various embodiments, the three-dimensional, engineered tissues are free of plasma, red blood cells, platelets, and the like and/or endogenously-generated plasma, red blood cells, platelets, and the like. In certain embodiments, the tissues lack hemoglobin. In some embodiments, the tissues lack innervation or neurons. In some embodiments, the tissue lack neuronal markers such as any of: Beat III tubulin, MAP2, NeuN and neuron specific enolase. In some embodiments, the engineered tissues are species chimeras, wherein at least one cell or cell-type of the tissue is from a different mammalian species then another cell or cell-type of the tissue. In some embodiments, the tissues described herein are marked by an increased basal metabolic rate then tissue in vivo or ex vivo. In some embodiments, the tissues described herein are marked by an increased proliferative rate then tissue in vivo or in ex vivo culture. In some embodiments, the tissues described herein are marked by an increased cell size when compared to cells in tissue in vivo or in ex vivo culture.

The tissues of the current disclosure are marked by extended viability in culture. Tissue explants exhibit low viability in in vitro culture. In certain embodiments, the three-dimensional, engineered tissues described herein are viable after 7 days in culture. In certain embodiments, the three-dimensional, engineered tissues described herein are viable after 10 days in culture. In certain embodiments, the three-dimensional, engineered tissues described herein are viable after 14 days in culture. In certain embodiments, the three-dimensional, engineered tissues described herein are viable after 21 days in culture.

One advantage of the tissues fabricated by the methods of this disclosure is the ability to form novel and advantageous chimeras. In some embodiments, the engineered tissues are species chimeras, wherein at least one cell or cell-type of the tissue is from a different mammalian species than another cell or cell-type of the tissue. For example, the dermal bio-ink contains a cell of mouse, rat, or primate origin and the epidermal bio-ink contains a cell of human origin. In some embodiments, the engineered tissues are genetic chimeras, wherein at least one cell or cell-type is from a different genetic background than the genetic background of any other cell or cell-type of the tissue. For example, the dermal fibroblasts of the dermal bio-ink may be from a certain donor and the keratinocytes or melanocytes of the epidermal bio-ink may be from a different donor, creating a genetic chimera. In some embodiments, the engineered tissues are chimeras of other types. For example, the dermal bio-ink may comprise a transformed dermal fibroblast, and the epidermal bio-ink may comprise a primary untransformed keratinocyte or melanocyte. In certain embodiments, the dermal bio-ink may contain fibroblasts of non-dermal origin. In certain embodiments, the tissues are free of immune cells. In certain embodiments, the tissues are free of Langerhans cells. In certain embodiments, the tissues are free of T-cells. In certain embodiments, the tissues are substantially free of any of the immune cells marked by expression of the following proteins: CD11c, DC-SIGN, CD11b, CD4, CD8, CD28, CD3, CD19 CD80 or CD86.

In some embodiments, one or more components of the engineered tissues described herein are bioprinted, which comprises an additive fabrication process. Therefore, in such embodiments, through the methods of fabrication, the fabricator exerts significant control over the composition of the resulting engineered tissues described herein. As such, the engineered tissues described herein optionally comprise any of the layers, structures, compartments, and/or cells of native tissue. Conversely, the engineered skin tissues described herein optionally lack any of the layers, structures, compartments, and/or cells of native tissue.

Bioprinting

The tissues and methods described herein involve bio-ink formulations and bioprinting methods to create 3D tissue structures containing compositions of living cells. The printing methods utilize bio-ink to create geometries which produce layers to mimic native tissue. In various embodiments, the printing methods utilize a variety of printing surfaces with a variety of pore sizes that are optionally coated with matrix support material such as collagen. In some embodiments, the printing surface can be static or flexible. The flexible printing surface allows printed tissue to be subjected to flexing and other non-static conditions post fabrication. In some embodiments, hydrogels are optionally added to support biomaterials or to constitute space-saving regions in which there are no cells.

In some embodiments, the engineered tissues, arrays, and methods described herein incorporate continuous deposition printing into a 3D tissue model. Continuous deposition is optionally utilized to produce single or multiple layers. In one embodiment, a bio-ink comprised of fibroblasts is printed to produce a tissue mimicking the dermis. In another embodiment, bio-ink comprised of keratinocytes or a mixture of keratinocytes and melanocytes is printed to produce a tissue to mimic the epidermis. A third embodiment combines bio-inks to simultaneously deposit the epidermal bio-ink on top of the dermal bio-ink. Continuous deposition printing provides an advantage to current 3D tissue models in that it enables cells to be placed within a precise geometry and enables the use of multiple bio-ink formulations including, but not limited to, inert gels such as NOVOGEL 2.0 and NOVOGEL 3.0, and cell paste. Continuous deposition allows optional incorporation of various biomaterials into the NOVOGEL formulation and various printing surfaces to promote extracellular matrix production and differentiation.

Aerosol spray bioprinting techniques allow for the spray of materials that include, for example, a cell suspension, media, bio-ink, biosupport material, or a combination thereof. In some embodiments, the engineered tissues and methodologies described herein highlight the ability to aerosol spray (e.g., spray) single cells at a resolution of one cell layer thickness and the ability to spray cell aggregates. The sprayed layer could, however, also be modified by changing parameters including but not limited to spray material velocity, distance, time, volume, and viscosity. For the creation of the epidermal layer, cells are optionally sprayed onto other bioprinted layers to result in a full-thickness model, or directly onto transwell or other matrix coated surfaces to specifically generate an epidermal model. The spray method is optionally utilized to embed sprayed material into a soft surface such as biosupport material or NOVOGEL. For example, a dermal layer could be created by spraying fibroblasts into a collagen gel.

The aerosol spray method is unique when compared to continuous deposition printing in that it does not require a flat printing surface, such as a transwell membrane, to zero the initial printing position in the x, y, and z-axes. The aerosol spray method is optionally used to apply a layer to an uneven surface such as a structure previously printed by continuous deposition.

Figure 1:
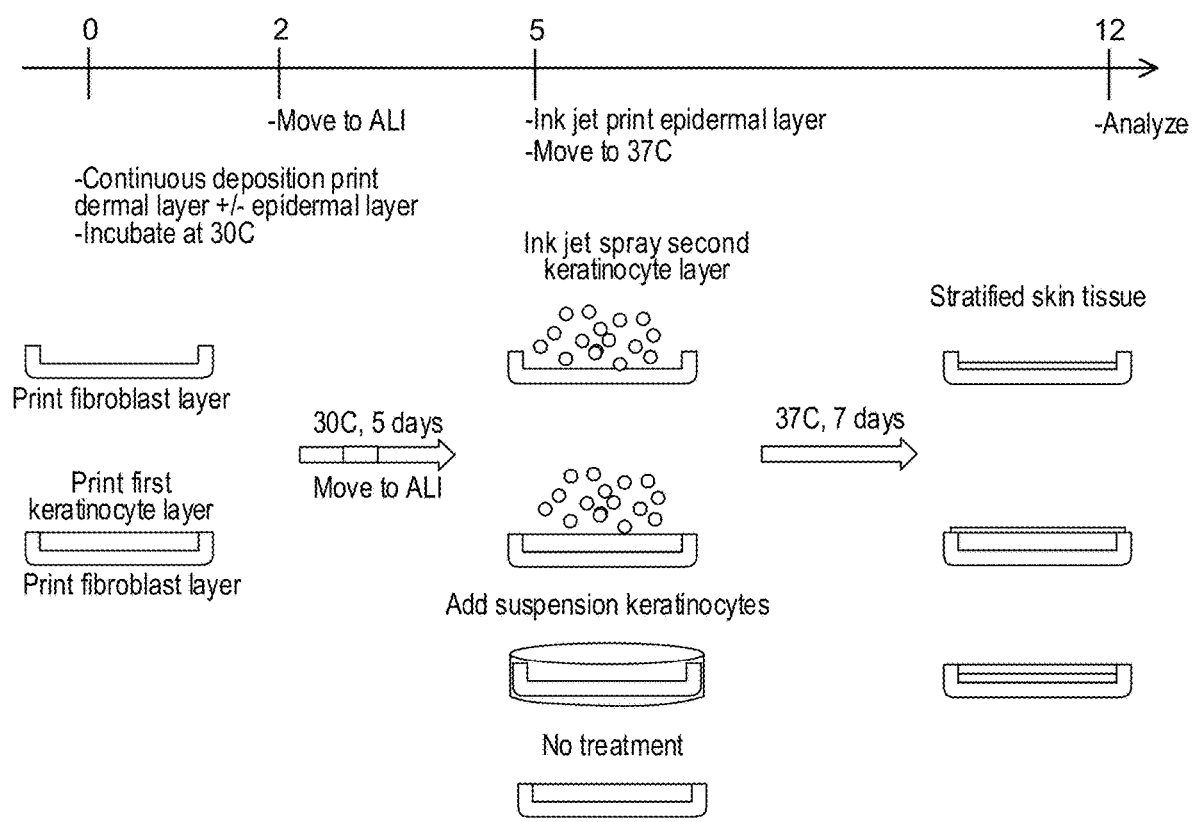
FIG. 1 shows a non-limiting example of an experimental design; in this case, an experimental design depicting a variety of bioprinting techniques used to achieve the engineered tissues described herein.

Regardless of the printing method used, a variety of factors are optionally modified to promote proliferation and/or differentiation of bioprinted tissue cells. In some cases, dermal media, epidermal media, or a combination of dermal and epidermal media is added to the tissue constructs. In addition, the media composition is optionally changed at different points in the tissue lifetime to promote the desired biology. The tissue constructs are optionally moved to an air liquid interface or subjected to atmospheric changes such as modification of humidity or $CO_2$. A hypothetical experimental design combining both printing approaches is shown in FIG. 1.

In some embodiments, at least one component of the three dimensional engineered biological tissues/constructs are bioprinted. In further embodiments, bioprinted constructs are made with a method that utilizes a rapid prototyping technology based on three-dimensional, automated, computer-aided deposition of cells, including cell solutions, cell suspensions, cell-comprising gels or pastes, cell concentrations, multicellular bodies (e.g., cylinders, spheroids, ribbons, etc.), and, optionally, confinement material onto a biocompatible support surface (e.g., composed of hydrogel and/or a porous membrane) by a three-dimensional delivery device (e.g., a bioprinter). In some aspects, the surface can be a layer of cells previously printed. In some aspects, the surface can be a cell-free biocompatible surface. As used herein, in some embodiments, the term "engineered," when used to refer to tissues and/or organs means that cells, cell solutions, cell suspensions, cell-comprising gels or pastes, cell concentrates, multicellular aggregates, and layers thereof are positioned to form three-dimensional structures by a computer-aided device (e.g., a bioprinter) according to a computer script. In further embodiments, the computer script is, for example, one or more computer programs, computer applications, or computer modules. In still further embodiments, three-dimensional tissue structures form through the post-printing fusion of cells or multicellular bodies which, in some cases, is similar to self-assembly phenomena in early morphogenesis.

While a number of methods are available to arrange cells, multicellular aggregates, and/or layers thereof on a biocompatible surface to produce a three-dimensional structure including manual placement, positioning by an automated, computer-aided machine such as a bioprinter is advantageous. Advantages of delivery of cells or multicellular bodies with this technology include rapid, accurate, and reproducible placement of cells or multicellular bodies to produce constructs exhibiting planned or pre-determined orientations or patterns of cells, multicellular aggregates and/or layers thereof with various compositions. Advantages also include assured high cell density, while minimizing cell damage.

In some embodiments, the method of bioprinting is continuous and/or substantially continuous. A non-limiting example of a continuous bioprinting method is to dispense bio-ink (i.e., cells, cells combined with an excipient or extrusion compound, or aggregates of cells) from a bioprinter via a dispense tip (e.g., a syringe, needle, capillary tube, etc.) connected to a reservoir of bio-ink. In further non-limiting embodiments, a continuous bioprinting method is to dispense bio-ink in a repeating pattern of functional units. In various embodiments, a repeating functional unit has any suitable geometry, including, for example, circles, squares, rectangles, triangles, polygons, and irregular geometries, thereby resulting in one or more tissue layers with planar geometry achieved via spatial patterning of distinct bio-inks and/or void spaces. In further embodiments, a repeating pattern of bioprinted function units comprises a layer and a plurality of layers are bioprinted adjacently (e.g., stacked) to form an engineered tissue or organ with laminar geometry. In various embodiments, 2, 3, 4, 5, 6, 7, 8, 9, 10, 11, 12, 13, 14, 15, or more layers are bioprinted adjacently (e.g., stacked) to form an engineered tissue or organ. In further embodiments, one or more layers of a tissue with laminar geometry also has planar geometry.

In some embodiments, the method of bioprinting is discontinuous. A non-limiting example of discontinuous bioprinting is when bio-ink or cells are dispensed, and then the flow of bio-ink or cells is stopped, paused for a certain amount of time, and then started again. This can allow for different bio-inks or cells, or the same bio-inks or cells to be layered with a delay in printing of the layers. In some embodiments, the discontinuous bioprinting is achieved using an aerosol spray type of bioprinting, wherein cells are applied to an existing tissue layer or surface using an aerosol spray technology. In some embodiments, a single layer or plurality of layers of cells including dermal cells and cell matrix components or bio-inks are deposited, followed by a temporal delay in deposition of a single layer or plurality of layers epidermal cells or bio-inks. In some embodiments, the deposition of the epidermal cells is by an aerosol spray.

In certain embodiments, deposition of a second bio-ink occurs after deposition of a first bio-ink. In certain embodiments, deposition of the second bio-ink is temporally delayed before it is deposited on the first bio-ink. In certain embodiments, the delay is greater than 1, 2, 3, 4, 5, 6, 7, 8, 9, milliseconds. In certain embodiments, the delay is greater than 10 milliseconds. In certain embodiments, the delay is greater than 20, 30, 40, 50, 60, 70, 80, 90 or 100, milliseconds. In certain embodiments, the delay is greater than 200, 300, 400, 500, 600, 700, 800, 900 or 1000, milliseconds. In certain embodiments, the delay is greater than 1, 2, 3, 4, 5, 6, 7, 8, 9, 10 seconds. In certain embodiments, the delay is greater than 10, 20, 30, 40, 50, or 60 seconds. In certain embodiments, the delay is greater than 1, 2, 3, 4, 5, 6, 7, 8, 9, or 10 minutes. In certain embodiments, the delay is greater than 10, 20, 30, 40, 50, or 60 minutes. In certain embodiments, the delay is greater than 1, 2, 3, 4, 5, 6, 7, 8, 9, 10, 11, 12, 13, 14, 15, 16, 17, 18, 19, 20, 21, 22, 23, or 24 hours. In certain embodiments, the delay is greater than 1, 2, 3, 4, 5, 6, or 7 days. In certain embodiments, the delay is greater than 1, 2, 3, or 4 weeks. In certain embodiments, the delay is less than 1, 2, 3, 4, 5, 6, 7, 8, 9, milliseconds. In certain embodiments, the delay is less than 10 milliseconds. In certain embodiments, the delay is less than 20, 30, 40, 50, 60, 70, 80, 90 or 100, milliseconds. In certain embodiments, the delay is less than 200, 300, 400, 500, 600, 700, 800, 900 or 1000, milliseconds. In certain embodiments, the delay is less than 1, 2, 3, 4, 5, 6, 7, 8, 9, 10 seconds. In certain embodiments, the delay is less than 10, 20, 30, 40, 50, or 60 seconds. In certain embodiments, the delay is less than 1, 2, 3, 4, 5, 6, 7, 8, 9, or 10 minutes. In certain embodiments, the delay is less than 10, 20, 30, 40, 50, or 60 minutes. In certain embodiments, the delay is less than 1, 2, 3, 4, 5, 6, 7, 8, 9, 10, 11, 12, 13, 14, 15, 16, 17, 18, 19, 20, 21, 22, 23, or 24 hours. In certain embodiments, the delay is less than 1, 2, 3, 4, 5, 6, or 7 days. In certain embodiments, the delay is less than 1, 2, 3, or 4 weeks.

Bio-Inks

Disclosed herein, in certain embodiments, are three-dimensional living tissues and methods for the fabrication of bioprinted tissue that maintains cellular compartments postfabrication without compromising cell viability and function. In some embodiments, cells are bioprinted by depositing or extruding bio-ink from a bioprinter. In some embodiments, "bio-ink" includes liquid, semi-solid, or solid compositions comprising a plurality of cells. In some embodiments, bio-ink comprises liquid or semi-solid cell solutions, cell suspensions, or cell concentrations. In further embodiments, a cell solution, suspension, or concentration comprises a liquid or semi-solid (e.g., viscous) carrier and a plurality of cells. In still further embodiments, the carrier is a suitable cell nutrient media, such as those described herein. In some embodiments, bio-ink comprises a plurality of cells that optionally cohere into multicellular aggregates prior to bioprinting. In further embodiments, bio-ink comprises a plurality of cells and is bioprinted to produce a specific planar and/or laminar geometry; wherein cohesion of the individual cells within the bio-ink takes place before, during and/or after bioprinting. In some embodiments, the bio-ink is produced by 1) collecting a plurality of cells in a fixed volume; wherein the cellular component(s) represent at least about 30, 40, 50, 60, 70, 80, 90% or 100% of the total volume. In some embodiments, bio-ink comprises semi-solid or solid multicellular aggregates or multicellular bodies. In further embodiments, the bio-ink is produced by 1) mixing a plurality of cells or cell aggregates and a biocompatible liquid or gel in a pre-determined ratio to result in bio-ink, and 2) compacting the bio-ink to produce the bio-ink with a desired cell density and viscosity. In some embodiments, the compacting of the bio-ink is achieved by centrifugation, tangential flow filtration ("TFF"), or a combination thereof. In some embodiments, the compacting of the bio-ink results in a composition that is extrudable, allowing formation of multicellular aggregates or multicellular bodies. In some embodiments, "extrudable" means able to be shaped by forcing (e.g., under pressure) through a nozzle or orifice (e.g., one or more holes or tubes). In some embodiments, the compacting of the bio-ink results from growing the cells to a suitable density. The cell density necessary for the bio-ink will vary with the cells being used and the tissue or organ being produced. In some embodiments, the cells of the bio-ink are cohered and/or adhered. In some embodiments, "cohere," "cohered," and "cohesion" refer to cell-cell adhesion properties that bind cells, multicellular aggregates, multicellular bodies, and/or layers thereof. In further embodiments, the terms are used interchangeably with "fuse," "fused," and "fusion." In some embodiments, the bio-ink additionally comprises support material, cell culture medium (or supplements thereof), extracellular matrix (or components thereof), cell adhesion agents, cell death inhibitors, anti-apoptotic agents, anti-oxidants, extrusion compounds, and combinations thereof.

In various embodiments, the cells are any suitable cell. In further various embodiments, the cells are vertebrate cells, mammalian cells, human cells, or combinations thereof. In some embodiments, the type of cell used in a method disclosed herein depends on the type of construct or tissue being produced. In some embodiments, the bio-ink comprises one type of cell (also referred to as a "homogeneous" or "monotypic" bio-ink). In some embodiments, the bio-ink comprises more than one type of cell (also referred to as a "heterogeneous" or "polytypic" bio-ink).

In some embodiments, the bio-ink comprises a cell culture medium. The cell culture medium is any suitable medium. In various embodiments, suitable cell culture media include, by way of non-limiting examples, Dulbecco's Phosphate Buffered Saline, Earle's Balanced Salts, Hanks' Balanced Salts, Tyrode's Salts, Alsever's Solution, Gey's Balanced Salt Solution, Kreb's-Henseleit Buffer Modified, Kreb's-Ringer Bicarbonate Buffer, Puck's Saline, Dulbecco's Modified Eagle's Medium, Dulbecco's Modified Eagle's Medium/Nutrient F-12 Ham, Nutrient Mixture F-10 Ham (Ham's F-10), Medium 199, Minimum Essential Medium Eagle, RPMI-1640 Medium, Ames' Media, BGJb Medium (Fitton-Jackson Modification), Click's Medium, CMRL-1066 Medium, Fischer's Medium, Glascow Minimum Essential Medium (GMEM), Iscove's Modified Dulbecco's Medium (IMDM), L-15 Medium (Leibovitz), McCoy's 5A Modified Medium, NCTC Medium, Swim's S-77 Medium, Waymouth Medium, William's Medium E, or combinations thereof. In some embodiments, the cell culture medium is modified or supplemented. In some embodiments, the cell culture medium further comprises albumin, selenium, transferrins, fetuins, sugars, amino acids, vitamins, growth factors, cytokines, hormones, antibiotics, lipids, lipid carriers, cyclodextrins, platelet-rich plasma, or a combination thereof.

In some embodiments, the bio-ink further comprises one or more components of an extracellular matrix or derivatives thereof. In some embodiments, "extracellular matrix" includes proteins that are produced by cells and transported out of the cells into the extracellular space, where they serve as a support to hold tissues together, to provide tensile strength, and/or to facilitate cell signaling. Examples, of extracellular matrix components include, but are not limited to, collagens, fibronectin, laminins, hyaluronates, elastin, and proteoglycans. For example, in some embodiments, the multicellular aggregates contain various ECM proteins (e.g., gelatin, fibrinogen, fibrin, collagens, fibronectin, laminins, elastin, and/or proteoglycans). The ECM components or derivatives of ECM components are optionally added to the cell paste used to form the multicellular aggregate. The ECM components or derivatives of ECM components added to the cell paste are optionally purified from a human or animal source, or produced by recombinant methods known in the art. Alternatively, the ECM components or derivatives of ECM components are naturally secreted by the cells in the elongate cellular body, or the cells used to make the elongate cellular body are optionally genetically manipulated by any suitable method known in the art to vary the expression level of one or more ECM components or derivatives of ECM components and/or one or more cell adhesion molecules or cell-substrate adhesion molecules (e.g., selectins, integrins, immunoglobulins, and adherins). In some embodiments, the ECM components or derivatives of ECM components promote cohesion of the cells in the multicellular aggregates. For example, gelatin and/or fibrinogen is suitably added to the cell paste, which is used to form multicellular aggregates. The fibrinogen is converted to fibrin by the addition of thrombin.

In some embodiments, the bio-ink further comprises an agent that inhibits cell death (e.g., necrosis, apoptosis, or autophagocytosis). In some embodiments, the bio-ink further comprises an anti-apoptotic agent. Agents that inhibit cell death include, but are not limited to, small molecules, antibodies, peptides, peptibodies, or combination thereof. In some embodiments, the agent that inhibits cell death is selected from: anti-TNF agents, agents that inhibit the activity of an interleukin, agents that inhibit the activity of an interferon, agents that inhibit the activity of an GCSF (granulocyte colony-stimulating factor), agents that inhibit the activity of a macrophage inflammatory protein, agents that inhibit the activity of TGF-B (transforming growth factor B), agents that inhibit the activity of an MMP (matrix metalloproteinase), agents that inhibit the activity of a caspase, agents that inhibit the activity of the MAPK/JNK signaling cascade, agents that inhibit the activity of a Src kinase, agents that inhibit the activity of a JAK (Janus kinase), or a combination thereof. In some embodiments, the bio-ink comprises an anti-oxidant. In some embodiments, the bio-ink comprises oxygen-carriers or other cell-specific nutrients.

In some embodiments, the bio-ink further comprises an extrusion compound (i.e., a compound that modifies the extrusion properties of the bio-ink). Examples of extrusion compounds include, but are not limited to gels, hydrogels, peptide hydrogels, amino acid-based gels, surfactant polyols (e.g., PLURONIC F-127 or PF-127), thermo-responsive polymers, hyaluronates, alginates, extracellular matrix components (and derivatives thereof), collagens, gelatin, other biocompatible natural or synthetic polymers, nanofibers, and self-assembling nanofibers. In some embodiments, extrusion compounds are removed after bioprinting by physical, chemical, or enzymatic means.

In certain embodiments, the bio-ink comprises between 50 million and 1 billion cells per milliliter. In certain embodiments, the bio-ink comprises between 50 million and 900 million cells per milliliter. In certain embodiments, the bio-ink comprises between 50 million and 800 million cells per milliliter. In certain embodiments, the bio ink comprises between 50 million and 700 million cells per milliliter. In certain embodiments, the bio ink comprises between 50 million and 600 million cells per milliliter. In certain embodiments, the bio ink comprises between 50 million and 500 million cells per milliliter. In certain embodiments, the bio ink comprises between 50 million and 400 million cells per milliliter. In certain embodiments, the bio ink comprises between 50 million and 300 million cells per milliliter. In certain embodiments, the bio ink comprises at least 1 million cells per milliliter. In certain embodiments, the bio ink comprises at least 10 million cells per milliliter. In certain embodiments, the bio ink comprises at least 50 million cells per milliliter. In certain embodiments, the bio ink comprises at least 100 million cells per milliliter. In certain embodiments, the bio ink comprises less than 100 million cells per milliliter. In certain embodiments, the bio ink comprises less than 10 million cells per milliliter. In certain embodiments, the bio ink comprises less than 5 million cells per milliliter. In certain embodiments, the bio ink comprises less than 1 million cells per milliliter.

In certain embodiments, the bio-ink is a viscous liquid. In certain embodiments, the bio-ink is a semi-solid. In certain embodiments, the bio-ink is a solid. In certain embodiments, the viscosity of the bio-ink is greater than 100 centipoise. In certain embodiments, the viscosity of the bio-ink is greater than 200 centipoise. In certain embodiments, the viscosity of the bio-ink is greater than 500 centipoise. In certain embodiments, the viscosity of the bio-ink is greater than 1,000 centipoise. In certain embodiments, the viscosity of the bio-ink is greater than 2,000 centipoise. In certain embodiments, the viscosity of the bio-ink is greater than 5,000 centipoise. In certain embodiments, the viscosity of the bio-ink is greater than 10,000 centipoise. In certain embodiments, the viscosity of the bio-ink is greater than 20,000 centipoise. In certain embodiments, the viscosity of the bio-ink is greater than 50,000 centipoise. In certain embodiments, the viscosity of the bio-ink is greater than 100,000 centipoise. In certain embodiments, the viscosity of the bio-ink is less than 100 centipoise. In certain embodiments, the viscosity of the bio-ink is less than 200 centipoise. In certain embodiments, the viscosity of the bio-ink is less than 500 centipoise. In certain embodiments, the viscosity of the bio-ink is less than 1,000 centipoise. In certain embodiments, the viscosity of the bio-ink is less than 2,000 centipoise. In certain embodiments, the viscosity of the bio-ink is less than 5,000 centipoise. In certain embodiments, the viscosity of the bio-ink is less than 10,000 centipoise. In certain embodiments, the viscosity of the bio-ink is less than 20,000 centipoise. In certain embodiments, the viscosity of the bio-ink is less than 50,000 centipoise. In certain embodiments, the viscosity of the bio-ink is less than 100,000 centipoise.

Cell Types

In some embodiments, any vertebrate cell is suitable for inclusion in bio-ink and the three dimensional engineered tissues. In further embodiments, the cells are, by way of non-limiting examples, contractile or muscle cells (e.g., skeletal muscle cells, cardiomyocytes, smooth muscle cells, and myoblasts), connective tissue cells (e.g., bone cells, cartilage cells, fibroblasts, and cells differentiating into bone forming cells, chondrocytes, or lymph tissues), bone marrow cells, endothelial cells, skin cells, epithelial cells, breast cells, vascular cells, blood cells, lymph cells, neural cells, Schwann cells, gut cells, gastrointestinal cells, liver cells, pancreatic cells, lung cells, tracheal cells, corneal cells, genitourinary cells, kidney cells, reproductive cells, adipose cells, parenchymal cells, pericytes, mesothelial cells, stromal cells, undifferentiated cells (e.g., embryonic cells, stem cells, and progenitor cells, adult stem cells, induced pluripotent stem cells (iPS cells), cancer stem cells), endoderm-derived cells, mesoderm-derived cells, ectoderm-derived cells, cells expressing disease associated antigen or associated with disease (e.g., cancer), and combinations thereof. In certain embodiments, the bio-ink or tissues comprise fibroblasts. In certain embodiments, the bio-ink or tissues comprise fibroblasts of dermal origin. In certain embodiments, the bio-ink or tissues comprise fibroblasts of renal origin. In certain embodiments, the bio-ink or tissues comprise fibroblasts of vascular origin. In certain embodiments, the bio-ink or tissues comprise endothelial cells. In certain embodiments, the bio-ink or tissues comprise fibroblasts and endothelial cells. In certain embodiments, the bio-ink or tissues comprise keratinocytes. In certain embodiments, the bio-ink or tissues comprise melanocytes. In certain embodiments, the bio-ink or tissues comprise hepatocytes. In certain embodiments, the bio-ink or tissues comprise stellate cells. In certain embodiments, the bio-ink or tissues comprise epidermal cells. In certain embodiments, the bio-ink or tissues comprise dermal cells. In certain embodiments, the bio-ink or tissues comprise epithelial cells. In certain embodiments, the bio-ink or tissues comprise renal tubular epithelial cells. In additional embodiments, the bio-inks or tissues consist essentially of a single cell type. In additional embodiments, the bio-inks or tissues consist essentially of two cell types. In additional embodiments, the bio-inks or tissues consist essentially of three cell types. In additional embodiments, the bio-inks or tissues consist essentially of four cell types. In additional embodiments, the bio-inks or tissues consist essentially of human cells. In additional embodiments, the bio-inks or tissues consist essentially of human primary cells.

In certain embodiments, the cells have been modified biologically, chemically or physically. Biological modifications include genetic modifications such as transfection, transduction, or infection with a transgene that encodes wild-type, dominant negative, truncated or mutant protein. The transgene can also encode an miRNA, siRNA, shRNA or an antisense RNA. The transgene can be maintained transiently or stably integrated into the cellular genome. Transfection can be achieved by cationic lipids, calcium phosphate, and electroporation, or through uptake of DNA without a specific transfection means. The cells can be virally transduced with any viral vector commonly used for these purposes such as a retrovirus, lentivirus, adenovirus, adeno associated virus, or vaccinia virus. The modification can be chemical such as treatment with a mutagen, antibiotic, antifungal, antiviral, HDAC inhibitor, chemotherapeutic, fluorescent labeling or tracking dyes, cell permanent or cell impermanent dyes. The modifications can be physical such as radiation, electromagnetic radiation, X-rays, and hot and cold shocks.

In some embodiments, the cells are adult, differentiated cells. In further embodiments, "differentiated cells" are cells with a tissue-specific phenotype consistent with, for example, a muscle cell, a fibroblast, or an endothelial cell at the time of isolation, wherein tissue-specific phenotype (or the potential to display the phenotype) is maintained from the time of isolation to the time of use. In other embodiments, the cells are adult, non-differentiated cells. In further embodiments, "non-differentiated cells" are cells that do not have, or have lost, the definitive tissue-specific traits of for example, muscle cells, fibroblasts, or endothelial cells. In some embodiments, non-differentiated cells include stem cells. In further embodiments, "stem cells" are cells that exhibit potency and self-renewal. Stem cells include, but are not limited to, totipotent cells, pluripotent cells, multipotent cells, oligopotent cells, unipotent cells, and progenitor cells. In various embodiments, stem cells are embryonic stem cells, adult stem cells, amniotic stem cells, and induced pluripotent stem cells. In other embodiments, the cells are a mixture of adult, differentiated cells and adult, non-differentiated cells.

Pre-Formed Scaffold

In some embodiments, disclosed herein are engineered, tissues that are free or substantially free of any pre-formed scaffold. In further embodiments, "scaffold" refers to synthetic scaffolds such as polymer scaffolds and porous hydrogels, non-synthetic scaffolds such as pre-formed extracellular matrix layers, dead cell layers, and decellularized tissues, and any other type of pre-formed scaffold that is integral to the physical structure of the engineered tissue and/or organ and not removed from the tissue and/or organ. In still further embodiments, decellularized tissue scaffolds include decellularized native tissues or decellularized cellular material generated by cultured cells in any manner; for example, cell layers that are allowed to die or are decellularized, leaving behind the ECM they produced while living.

In some embodiments, the engineered tissues/constructs and arrays thereof do not utilize any pre-formed scaffold, e.g., for the formation of the tissue, any layer of the tissue, or formation of the tissue's shape. As a non-limiting example, the engineered tissues of the present invention do not utilize any pre-formed, synthetic scaffolds such as polymer scaffolds, pre-formed extracellular matrix layers, or any other type of pre-formed scaffold at the time of manufacture or at the time of use. In some embodiments, the engineered tissues are substantially free of any pre-formed scaffolds. In further embodiments, the cellular components of the tissues contain a detectable, but trace or trivial amount of scaffold, e.g., less than 2.0%, less than 1.0%, or less than 0.5% of the total composition. In still further embodiments, trace or trivial amounts of scaffold are insufficient to affect long-term behavior of the tissue, or array thereof, or interfere with its primary biological function. In additional embodiments, scaffold components are removed post-printing, by physical, chemical, or enzymatic methods, yielding an engineered tissue that is free or substantially-free of scaffold components.

In some embodiments, the engineered tissues free, or substantially free, of pre-formed scaffold disclosed herein are in stark contrast to those developed with certain other methods of tissue engineering in which a scaffolding material is first formed, and then cells are seeded onto the scaffold, and subsequently the cells proliferate to fill and take the shape of the scaffold for example. In one aspect, the methods of bioprinting described herein allow production of viable and useful tissues that are free or substantially free of pre-formed scaffold. In another aspect, the cells of the invention are, in some embodiments, held in a desired three-dimensional shape using a confinement material. The confinement material is distinct from a scaffold at least in the fact that the confinement material is temporary and/or removable from the cells and/or tissue.

Hypothermic Hold

In certain embodiments, tissues are incubated or placed in a "hypothermic hold" at temperature below 24° C. for a certain time period after bioprinting. In certain embodiments, this temperature is greater than 0° C. In certain embodiments, this temperature is less than 24° C. In certain embodiments, this temperature is greater than 0° C. and less than 24° C. In certain embodiments, this temperature is greater than 0° C. and less than 20° C. In certain embodiments, this temperature is greater than 0° C. and less than 18° C. In certain embodiments, this temperature is greater than 0° C. and less than 16° C. In certain embodiments, this temperature is greater than 0° C. and less than 14° C. In certain embodiments, this temperature is greater than 0° C. and less than 12° C. In certain embodiments, this temperature is greater than 0° C. and less than 10° C. In certain embodiments, this temperature is greater than 0° C. and less than 8° C. In certain embodiments, this temperature is greater than 2° C. and less than 8° C. In certain embodiments, this temperature is greater than 2° C. and less than 10° C. In certain embodiments, this temperature is greater than 2° C. and less than 12° C. In certain embodiments, this temperature is greater than 2° C. and less than 8° C. In certain embodiments, this temperature is greater than 2° C. and less than 14° C. In certain embodiments, this temperature is greater than 2° C. and less than 16° C. In certain embodiments, this temperature is greater than 2° C. and less than 6° C. In certain embodiments, this temperature is about 1, 2, 3, 4, 5, 6, 7, 8, 9, 10, 11, 12, 13, 14, 15, 16, 17, 18, 19, 20, 21, 22, 23, or 24° C.

In certain embodiments, tissues and bio-inks are incubated at the hypothermic hold temperature for a certain amount of time. The time period of this incubation can be for at least 0.020, 0.05, 1, 2, 3, 4, 5, 6, 7, 8, 9, or 10 seconds. In certain embodiments, the time period of this incubation is at least 10, 20, 30, 40, 50, or 60, seconds. In certain embodiments, the time period of this incubation is at least 1, 2, 3, 4, 5, 6, 7, 8, 9, or 10 minutes. In certain embodiments, the time period of this incubation is at least 10, 20, 30, 40, 50, or 60 minutes. In certain embodiments, the time period of this incubation is at least 1, 2, 3, 4, 5, 6, 7, 8, 9, 10, 11, 12, 13, 14, 15, 16, 17, or 18 hours. In certain embodiments, the time period of this incubation is no more than 10, 20, 30, 40, 50, or 60, seconds. In certain embodiments, the time period of this incubation is no more than 1, 2, 3, 4, 5, 6, 7, 8, 9, or 10 minutes. In certain embodiments, the time period of this incubation is no more than 10, 20, 30, 40, 50, or 60 minutes. In certain embodiments, the time period of this incubation is no more than 1, 2, 3, 4, 5, 6, 7, 8, 9, 10, 11, 12, 13, 14, 15, 16, 17, or 18 hours.

In certain embodiments, the hypothermic hold is repeated. In certain embodiments, the hypothermic hold is repeated 1, 2, 3, 4, 5, 6, 7, 8, 9, 10, or more times. In certain embodiments, the hypothermic hold is repeated 10, 20, 30, 40, 50, 60, 70, 80, 90, or 100, or more times. In certain embodiments, the hypothermic hold is achieved by contacting the bio-ink to a bio-compatible liquid that is at a hypothermic temperature. In certain embodiments, the hold is achieved by contacting the bio-ink to a temperature controlled or "chilled" surface.

Low Temperature Incubation

In certain embodiments, the tissues are "matured" or incubated with a single low temperature of a combination at a low temperatures after bioprinting. A low-temperature is any temperature below 37° C. In certain embodiments, this step is independent of the aforementioned hypothermic hold. In certain embodiments, this step occurs after the aforementioned hypothermic hold. In certain embodiments, this step occurs without the aforementioned hypothermic hold. In certain embodiments, this temperature can be greater than 18° C. but less than 37° C. In certain embodiments, this temperature is about 24, 25, 26, 27, 28, 29, 30, 31, 32, 33, 34, 35, or 36° C. In certain embodiments, this temperature is greater than about 18° C., but less than 37° C. In certain embodiments, this temperature is greater than about 19° C., but less than 37° C. In certain embodiments, this temperature is greater than about 20° C., but less than 37° C. In certain embodiments, this temperature is greater than about 21° C., but less than 37° C. In certain embodiments, this temperature is greater than about 22° C., but less than 37° C. In certain embodiments, this temperature is greater than about 23° C., but less than 37° C. In certain embodiments, this temperature is greater than about 24° C., but less than 37° C. In certain embodiments, this temperature is greater than about 18° C., but less than 36° C. In certain embodiments, this temperature is greater than about 18° C., but less than 35° C. In certain embodiments, this temperature is greater than about 18° C., but less than 34° C. In certain embodiments, this temperature is greater than about 18° C., but less than 33° C. In certain embodiments, this temperature is greater than about 18° C., but less than 32° C. In certain embodiments, this temperature is greater than about 28° C., but less than 32° C.

In certain embodiments, the amount of time the tissue is incubated is for greater than 1 hour but less than 20 days. In certain embodiments, the amount of time the tissue is incubated is 1, 2, 3, 4, 5, 6, 7, 8, 9, 10, 11, 12, 13, 14, 15, 16, 17, 18, 19, 20, 21, 22, 23, or 24 hours. In certain embodiments, the amount of time is for 1, 2, 3, 4, 5, 6, 7, 8, 9, 10, 11, 12, 13, 14, 15, 18, 19, or 20 days. In certain embodiments, the amount of time the tissue is incubated is for greater than 2 hours. In certain embodiments, the amount of time the tissue is incubated is for greater than 4 hours. In certain embodiments, the amount of time the tissue is incubated is for greater than 8 hours. In certain embodiments, the amount of time the tissue is incubated is for greater than 12 hours. In certain embodiments, the amount of time the tissue is incubated is for greater than 16 hours. In certain embodiments, the amount of time the tissue is incubated is for greater than 24 hours. In certain embodiments, the amount of time the tissue is incubated is for greater than 3 days. In certain embodiments, the amount of time the tissue is incubated is for greater than 7 days.

Hydrogels

In certain embodiments, the tissues fabricated by the methods of this disclosure utilize hydrogels, examples include, but are not limited to, those derived from collagen, hyaluronate, hyaluronan, fibrin, alginate, agarose, chitosan, chitin, cellulose, pectin, starch, polysaccharides, fibrinogen/thrombin, fibrillin, elastin, gum, cellulose, agar, gluten, casein, albumin, vitronectin, tenascin, entactin/nidogen, glycoproteins, glycosaminoglycans (GAGs) and proteoglycans which may contain for example chrondroitin sulfate, fibronectin, keratin sulfate, laminin, heparan sulfate proteoglycan, decorin, aggrecan, perlecan and combinations thereof. In other embodiments, suitable hydrogels are synthetic polymers. In further embodiments, suitable hydrogels include those derived from poly(acrylic acid) and derivatives thereof, poly(ethylene oxide) and copolymers thereof, poly(vinyl alcohol), polyphosphazene, and combinations thereof. In various specific embodiments, hydrogel, NOVOGEL, agarose, alginate, gelatin, MATRIGEL, hyaluronan, poloxamer, peptide hydrogel, poly(isopropyl n-polyacrylamide), polyethylene glycol diacrylate (PEG-DA), hydroxyethyl methacrylate, polydimethylsiloxane, polyacrylamide, poly(lactic acid), silicon, silk, or combinations thereof.

Cross-Linkers

In certain embodiments, the tissues fabricated by the method of the disclosure do not require any cross-linking to form compartmentalized tissues. In certain embodiments, the tissues do not require chemical cross-linking, gluteraldehyde or bis-epoxide by way of non-limiting example. In certain embodiments, the tissues do not require cross-linking by ionic cross-linkers. In certain embodiments, the tissues do not require cross-linking by any cationic or anionic cross-linkers. In certain, embodiments, the tissues do not require cross-linking by calcium, magnesium, sodium, chloride, alginate, or any combination thereof. In certain, embodiments, the tissues do not require cross-linking by enzymatic cross-linkers. In certain embodiments, the cells do not require physical cross-linking. In certain embodiments, the tissues do not require photo cross-linking. In certain embodiments, the tissues do not require photo cross-linking or, radiation cross-linking, including ultraviolet or visible light.

Low Ionic Environments

In certain embodiments, the bioprinted tissues, bio-inks, and cells are exposed to divalent cationic cross-linking compounds such as calcium that do not exceed physiological levels. Physiological levels for this purpose are between 1 and 1.5 mM for ionic calcium, and between 2 and 3 mM for total calcium. In certain embodiments, the tissues or bio-inks are exposed to more than 1, 2, 3, 4, 5, 6, 7, 8, 9, 10 mM total calcium. In certain embodiments, the tissues or bio-inks are exposed to more than 5, 10, 15, 20, 25, 30, 35, 40, 45, or 50 mM total calcium. Calcium comprises all ionic species of calcium including, but not limited to, calcium chloride or calcium phosphate. In certain embodiments, the tissues or bio-inks are not exposed to other divalent cationic cross-linking compounds such as strontium, magnesium, barium, or other multivalent ions that may include copper, aluminum, or iron. In certain embodiments, the tissues or bio-inks are exposed to more than 1, 2, 3, 4, 5, 6, 7, 8, 9, or 10 mM of an ionic cross-linker. In certain embodiments, the tissues or bio-inks are exposed to more than 10, 20, 30, 40, 50, 60, 70, 80, 90, or 100 mM of an ionic cross-linker.

Reductions in Apoptosis

In certain embodiments, the bioprinted tissues fabricated by the methods of this disclosure, reduce apoptosis in the bioprinted tissues when compared to bioprinted tissues that are not bioprinted by the methods of this disclosure. In certain embodiments, apoptosis is reduced by 5%, 10%, 15%, 20%, 25%, 30%, 35%, 40%, 45%, 50%, 55%, 60%, 65%, 70%, 75%, 80%, 85%, 90%, or more. In certain embodiments, apoptosis is reduced by 10% or more. In certain embodiments, apoptosis is reduced by 25% or more. In certain embodiments, apoptosis is reduced by 30% or more. In certain embodiments, apoptosis is reduced by 50% or more. In certain embodiments, apoptosis is reduced by 70% or more. In certain embodiments, apoptosis is reduced by 90% or more. In certain embodiments, the reduction in apoptosis is measured by changes in molecular markers of apoptosis; non-limiting examples include DNA fragmentation, TUNEL staining, changes in activated caspase, changes in caspase cleavage products, changes in total caspase, changes in mRNA levels consistent with a reduction or increase in apoptosis, changes in cell surface markers of apoptosis (Anexin V, by way of non-limiting example). The changes in molecular markers can be measured by immunohistochemistry (IHC), flow cytometry, western blot, PCR including real-time PCR, or any homogenous caspase assay including ones that are commercially available.

In certain embodiments, disclosed herein are systems of tissues with improved viability and utility for in vitro and therapeutic applications. In certain embodiments, enclosed herein are arrays of tissues with improved viability and utility for in vitro and therapeutic applications. An array is an in vitro association of multiple tissues that allows for enhanced screening of compounds for potential use as therapeutics. In certain embodiments, the arrays or systems allow for at least 20 µm of space between tissues. In certain embodiments, the array or systems allow for at least 100 µm of space between tissues. In certain embodiments, the array or systems allow for at least 1000 µm of space between tissues. In certain embodiments, the tissues for use in the arrays or systems are compositionally the same. In certain embodiments, the tissues for use in the arrays or systems are compositionally different. In certain embodiments, the tissues for use in the arrays or systems are attached to a biocompatible surface. In certain embodiments, the tissues for use in the arrays or systems are anchored to a biocompatible surface. Attachment can be through physical means or by cell-adhesion molecules coated on the biocompatible surface. In certain embodiments, attachment is through secretion of cell adhesion proteins or molecules by the cells that are deposited.

The disclosure herein includes business methods. In some embodiments, the speed and scalability of the techniques and methods disclosed herein are utilized to design, build, and operate industrial and/or commercial facilities for production of engineered tissues and/or organs for engraftment or use in generation of cell-based tools for research and development, such as in vitro assays. In further embodiments, the engineered tissues and/or organs and arrays thereof are produced, stored, distributed, marketed, advertised, and sold as, for example, cellular arrays (e.g., microarrays or chips), tissue arrays (e.g., microarrays or chips), and kits for biological assays, high-throughput drug screening, toxicology and toxicity testing. In other embodiments, the engineered tissues and/or organs and arrays thereof are produced and utilized to conduct biological assays and/or drug screening as a service. In other embodiments, the business methods involve on demand bioprinting of tissues for use in transplantation.

EXAMPLES

Example 1—Incubation Below 37° C. Improves Skin Tissue Formation

Procedures

Bio-ink was generated by a cellular mixture of 100% primary adult human dermal fibroblasts (HDFa) in 6% gelatin (NOVOGEL 2.0) in a concentration of 150 million cells per milliliter.

Three-dimensional bio-ink constructs were printed by continuous deposition using the NOVOGEN BIOPRINTER platform in a 4 mm×4 mm×0.5 mm base sheet with a 1 mm wall bordering the top to create a dermal structure resembling a cup. One tissue construct was printed per transwell in a 6 well plate. The transwell printing surface contained a polytetrafluoroethylene (PTFE) membrane coated with equimolar mixture of types I and III collagen (bovine) with pores 3 µm in size.

Epidermal cell paste containing a mixture of 95% primary adult human epidermal keratinocytes (HEKa) and 5% primary adult human epidermal melanocytes (HEMa) was then printed on top of the dermal bio-ink immediately or between 0.020 seconds and several hours or several days.

Cell paste was measured post print at 90.5% viable by trypan exclusion assay. Cell number in deposited epidermal layer was estimated at 160,000 cells by cell counting on a CELLOMETER.

Media was then added to the outer well of the transwell in a volume of 2 ml. The media used for subsequent growth and maintenance of the skin tissue was a 50:40:10 ratio of HDFa:HEKa:HEMa media. The volume added was sufficient to collect at the base of the printed structure but not to submerge the structure. Media was changed 48 hours later and subsequently changed daily after that.

Printed constructs were placed into a non-humidified incubator at 30° C. for 5 days. This is a key step that enables maintenance of tissue shape for a period of maturation. After 5 days, the temperature was raised to 37° C. for an additional 7 days.

At days 2, 9, and 12, constructs were either lysed for RNA analysis or fixed in 2% PFA for histological analysis.

Results

Figure 2:
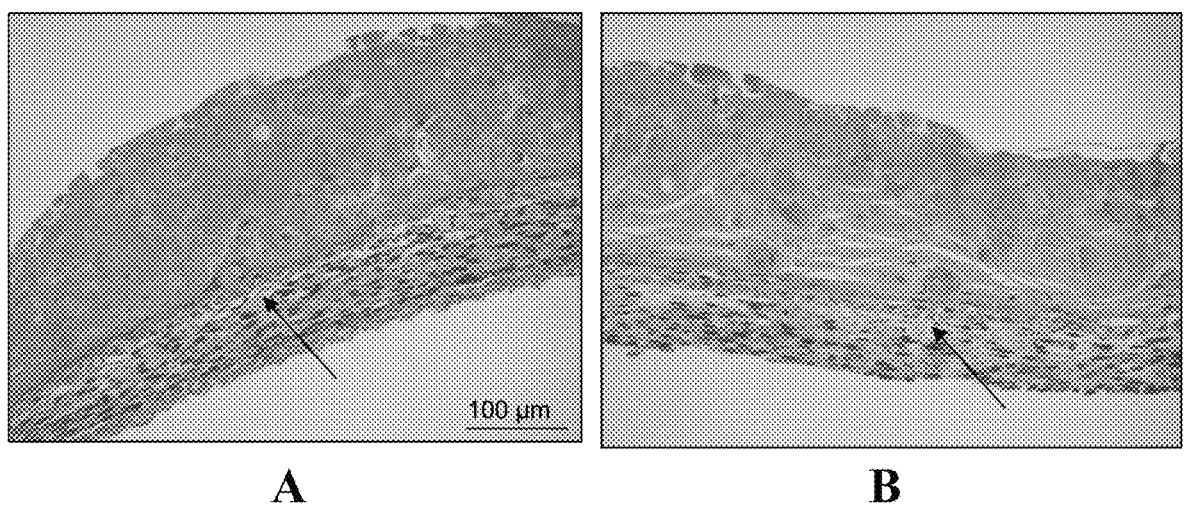
FIG. 2 shows non-limiting examples of photomicrographs of engineered skin tissues; in this case, photomicrographs depicting H&E staining of two of the tissues of Example 1 at day 12 post printing (first tissue: A; second tissue B) (arrows indicate distinct basal layer).
Figure 3:
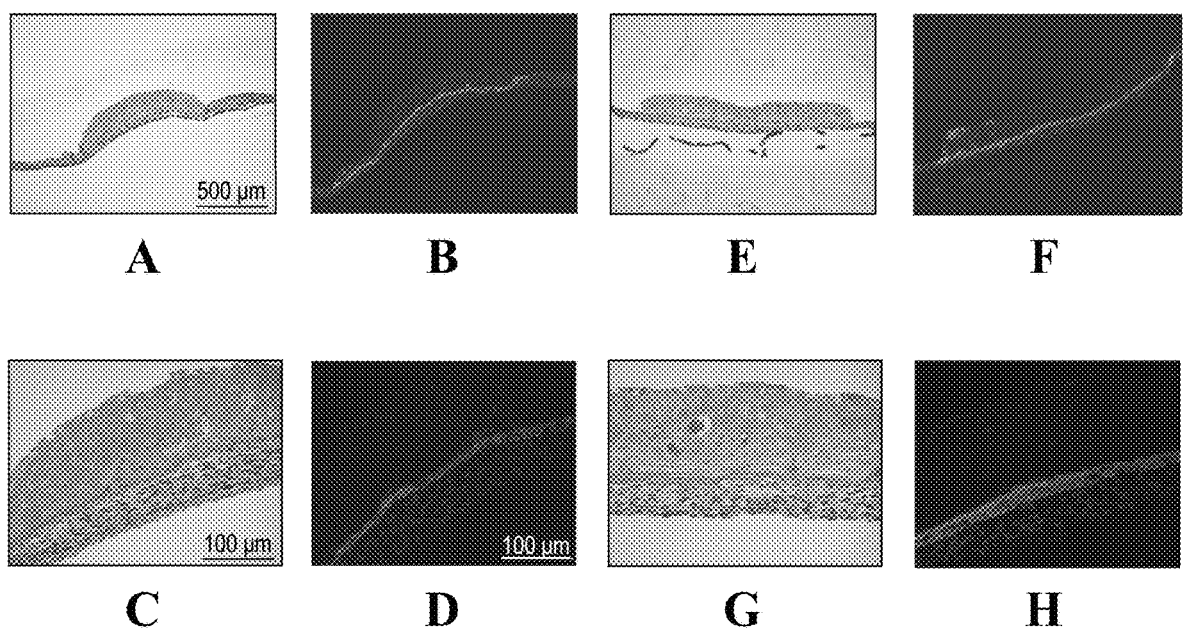
FIG. 3 shows non-limiting examples of photomicrographs of engineered skin tissues; in this case, photomicrographs depicting H&E staining (A, C, E, and G) and immunohistochemistry for visualization of CK14 (B, D, F, and H) of two of the tissues of Example 1 at day 12 post printing (first tissue: A-D; second tissue E-H).

H&E staining of skin tissues at day 12 shows a distinct layered architecture (FIGS. 2 and 3). Fibroblasts in a dermal layer are observed at the base (purple) and differentiated keratinocytes in an epidermal layer (pink) on top. An unexpected finding with this approach is the extent of the layered architecture observed. In particular, there is a layer of cells with distinct morphology can be observed at the interface (arrows). This layer stains specifically for CK14, indicating that the keratinocyte cells in the deposited paste have arranged into a basal layer.

Figure 4:
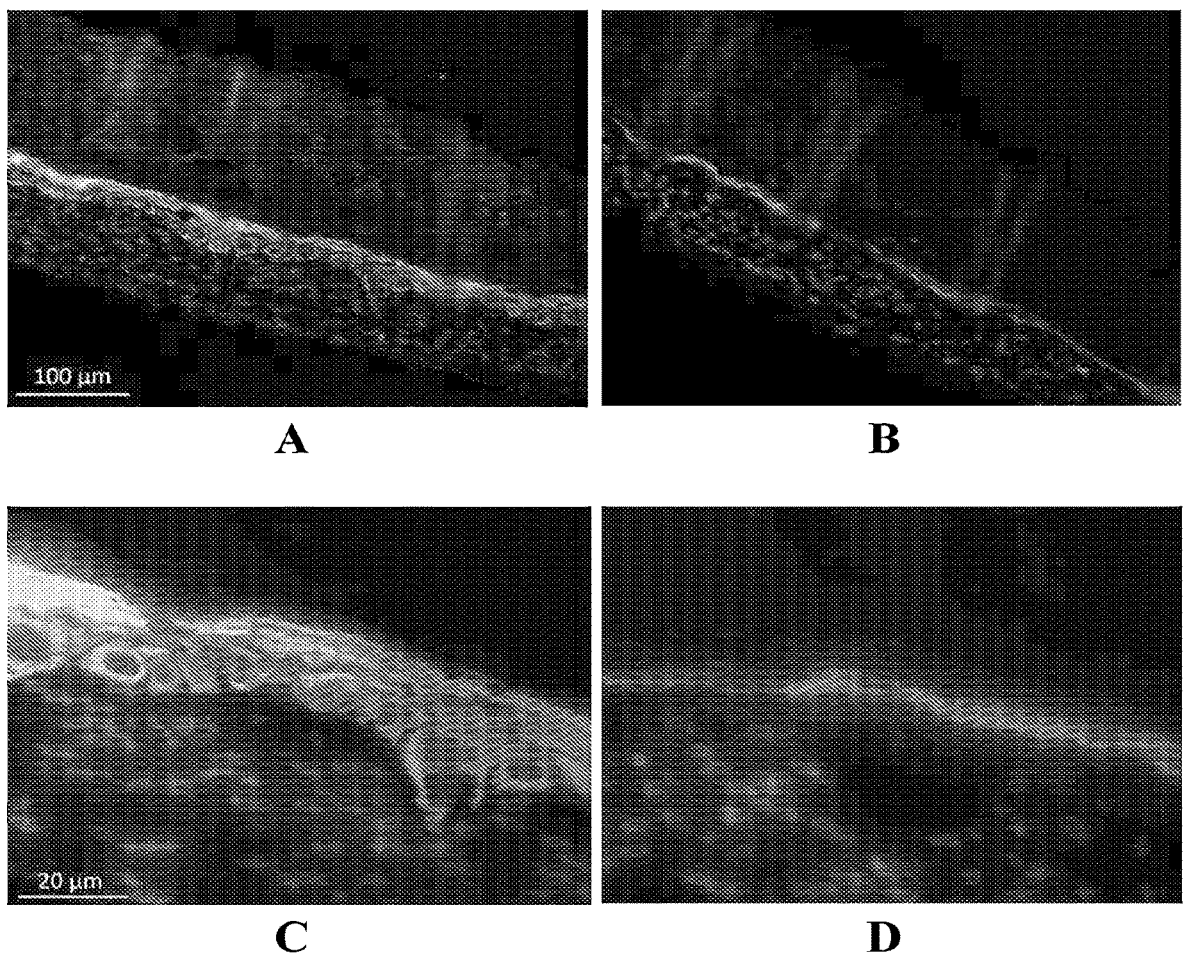
FIG. 4 shows non-limiting examples of photomicrographs of engineered skin tissues; in this case, photomicrographs depicting immunohistochemistry for visualization of CK5/IVL/Dapi (A and C) and CK10/Dapi (B and D) of a third tissue of Example 1 at day 12 post printing.

Distinct layers of differentiated keratinocytes are visualized by simultaneously staining for a basal cell marker CK5 and involucrin (IVL), a later stage differentiation marker of granular and cornified keratinocytes. Similar to normal human skin, differences in morphology are seen as basal cells appear to have a distinct cuboidal morphology, while differentiated keratinocytes on top appear flatter. The layered architecture also includes CK10-positive spinous and granular keratinocytes in mid stages differentiation (FIG. 4).

Although previous print methods have resulted in CK14 positive staining of the epidermal layer, the observed pattern is widespread throughout the layer and non-specific to a basal region at day 10. In the current approach, what is unexpected is that the staining is limited to a defined region at the base of the epidermal layer similar to native human skin at day 12 (FIG. 5).

Figure 6:
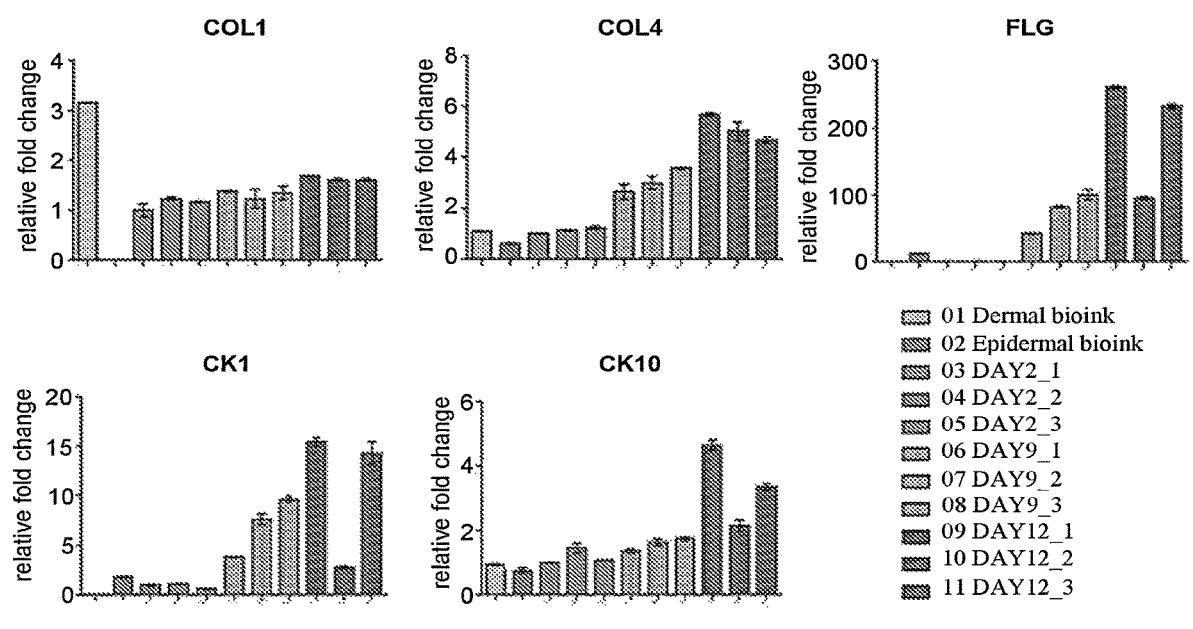
FIG. 6 shows exemplary experimental data on gene expression within the engineered skin tissues described herein in Example 1; in this case, a gene expression data for collagen (COL1 and COL4), filaggrin (FLG), and cytokeratin (CK1 and CK10).

Gene expression analysis supports histological findings. Data shows an increase in epidermal differentiation markers CK1, CK10, and especially late marker FLG over time. Gene expression also shows that collagen 4 levels increase over time, suggesting formation of a basement membrane. Collagen I levels are maintained over the time course of the experiment suggesting dermal layer remains viable (FIG. 6).

Example 2—Transient Exposure at 4° C. and Incubation Below 37° C. Improves Skin Tissue Formation Procedures Bio-ink was generated by a cellular mixture of 100% primary adult human dermal fibroblasts (HDFa) in 8% gelatin (NOVOGEL) in a concentration of 100 million cells per milliliter. The cell:gelatin ratio was altered to reduce the cellular density of the dermal sheet to better mimic dermal tissue in native skin.

Three-dimensional bio-ink constructs were printed by continuous deposition using the NOVOGEN BIOPRINTER platform in a 4 mm×4 mm×0.5 mm base sheet to create a dermal structure resembling a sheet. One tissue construct was printed per transwell—in a 6 well plate. The transwell printing surface contained a polytetrafluoroethylene (PTFE) membrane coated with equimolar mixture of types I and III collagen (bovine) with pores 3 µm in-size.

Epidermal cell paste containing a mixture of 100% primary neonatal human epidermal keratinocytes (HEKn) was then printed on top of the dermal bio-ink. A separate but identical epidermal paste structure was simultaneously deposited next to the dermal sheet directly onto the transwell printing surface. This structure was only comprised of epidermal keratinocyte paste and contained no dermal tissue.

Cell paste was measured post print at 87.1% viable by trypan exclusion assay. Cell number in deposited epidermal layer was estimated at 60,000 cells by cell counting on a CELLOMETER. Immediately following the print, constructs were placed in 4° C. for 10 minutes. This is a key step to harden the NOVOGEL, which helps to maintain the printed shape and improve construct to construct uniformity.

Cold media was then added to the outer well of the transwell in a volume of 3 ml. The media used for subsequent growth and maintenance of the skin tissue was a 50:50 ratio of HDFa:HEKn media. The initial volume added was sufficient to submerge the structure. All subsequent media changes used warmed media (30-37° C.) added to the outer well of the transwell and not to the inner basket. Media was changed 48 hours later and reduced to a volume of 1.5 ml per well to bring the structure to an air-liquid interface (ALI). Media and subsequently changed 48 hours after that (day 4) at a volume of 1.5 ml. On day 5, media was changed and further reduced to 1 ml per well and subsequently changed daily Printed constructs were placed into a non-humidified incubator at 30° C. for 5 days. This is a key step that enables maintenance of tissue shape for a period of maturation. After 5 days, the temperature was raised to 37° C. for an additional 7 days.

At days 0 and 12, constructs were either lysed for RNA analysis or fixed in 2% PFA for histological analysis.

Results

Figure 7:
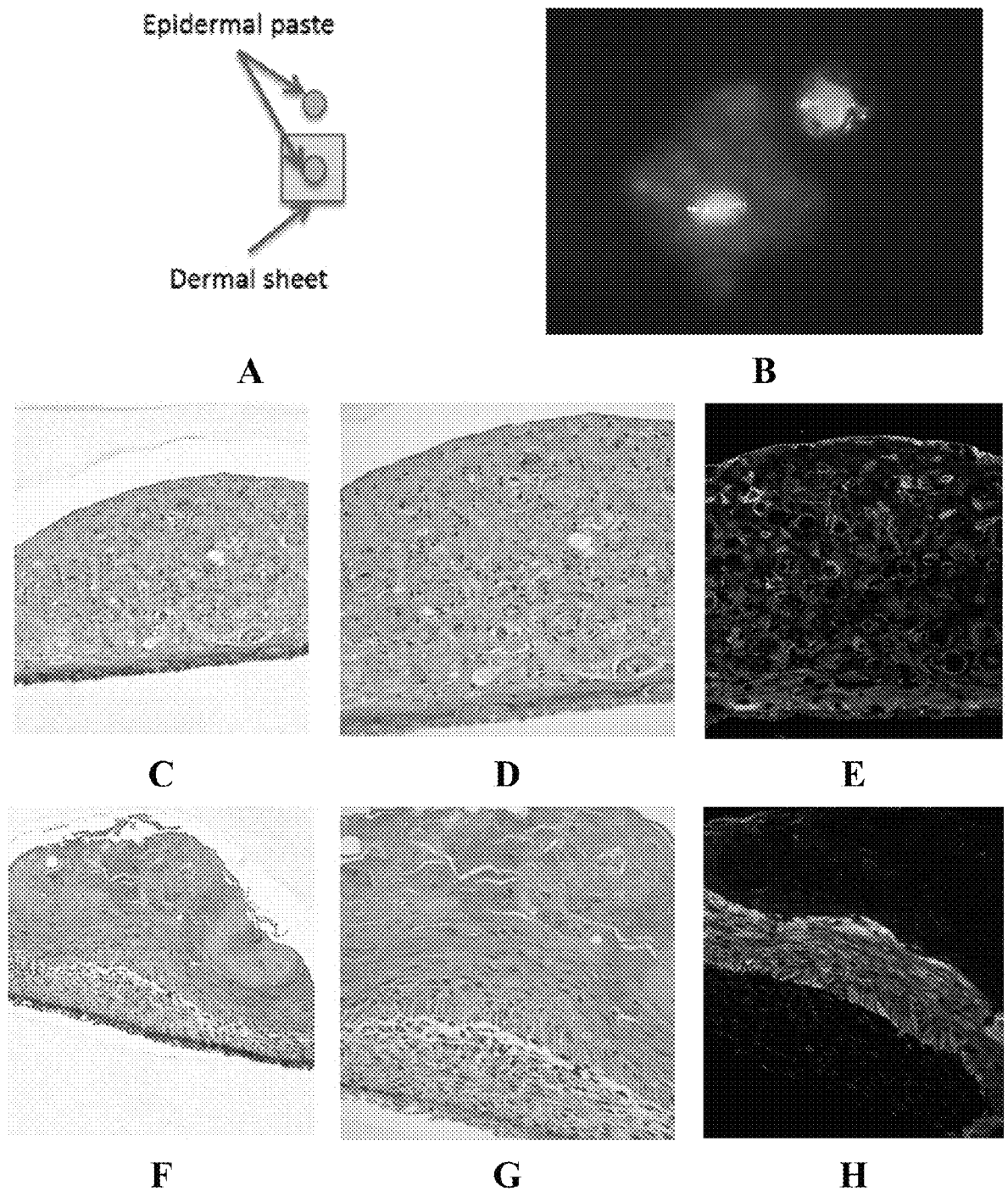
FIG. 7 shows the effect that dermal tissue has on epidermal organization and differentiation. (A) Is a schematic of the experiment of Example 2. (B) Shows macroscopic views of the printed tissue. (C and F) low magnification of H&E stained cells printed without (C) or with (F) dermal paste. (D and G) higher magnification of H&E stained cells printed without (D) or with (G) dermal paste. Distinct layers of differentiated keratinocytes are visualized by simultaneously staining for a basal cell marker CK5 (green) and involucrin (IVL, red), a later stage differentiation marker of granular and cornified keratinocytes in cells printed without (E) or with dermal paste (H).

Subsequent histological analysis to compare epidermal layer patterning of paste that had been printed on top of a dermal sheet versus directly onto the transwell surface yielded unexpected findings (FIGS. 7A and B). H&E staining of skin tissues at day 12 shows a distinct layered architecture only in structures with epidermal paste printed on top of a dermal layer (FIGS. 7 C and D versus F and G, FIG. 8A). Fibroblasts in a dermal layer are observed at the base (purple) and differentiated keratinocytes in an epidermal layer (pink) on top. In particular, there is a layer of cells with distinct morphology that can be observed at the interface. Distinct layers of differentiated keratinocytes are visualized by simultaneously staining for a basal cell marker CK5 (green) and involucrin (IVL, red), a later stage differentiation marker of granular and cornified keratinocytes (FIG. 7E versus H, FIG. 8B). The distinct green layer indicates that the keratinocyte cells in the deposited paste have arranged into a basal layer with a layer of more differentiated IVL positive cells on top. Similar to normal human skin, differences in morphology are seen as basal cells that appear to have a distinct cuboidal morphology, while differentiated keratinocytes on top appear flatter.

Staining for the proliferation marker PCNA (FIG. 8E, green) indicates that proliferation is high in both dermal fibroblasts and basal layer keratinocytes but not in differentiating keratinocytes. This pattern is similar to that which is found in native skin. Staining for apoptosis by TUNEL (FIG. 8F) also low showing very few positive staining cells in either dermal or epidermal layer. Collectively PCNA and TUNEL staining demonstrate that both dermal and epidermal compartments of the full thickness tissue are viable at day 12.

Figure 9:
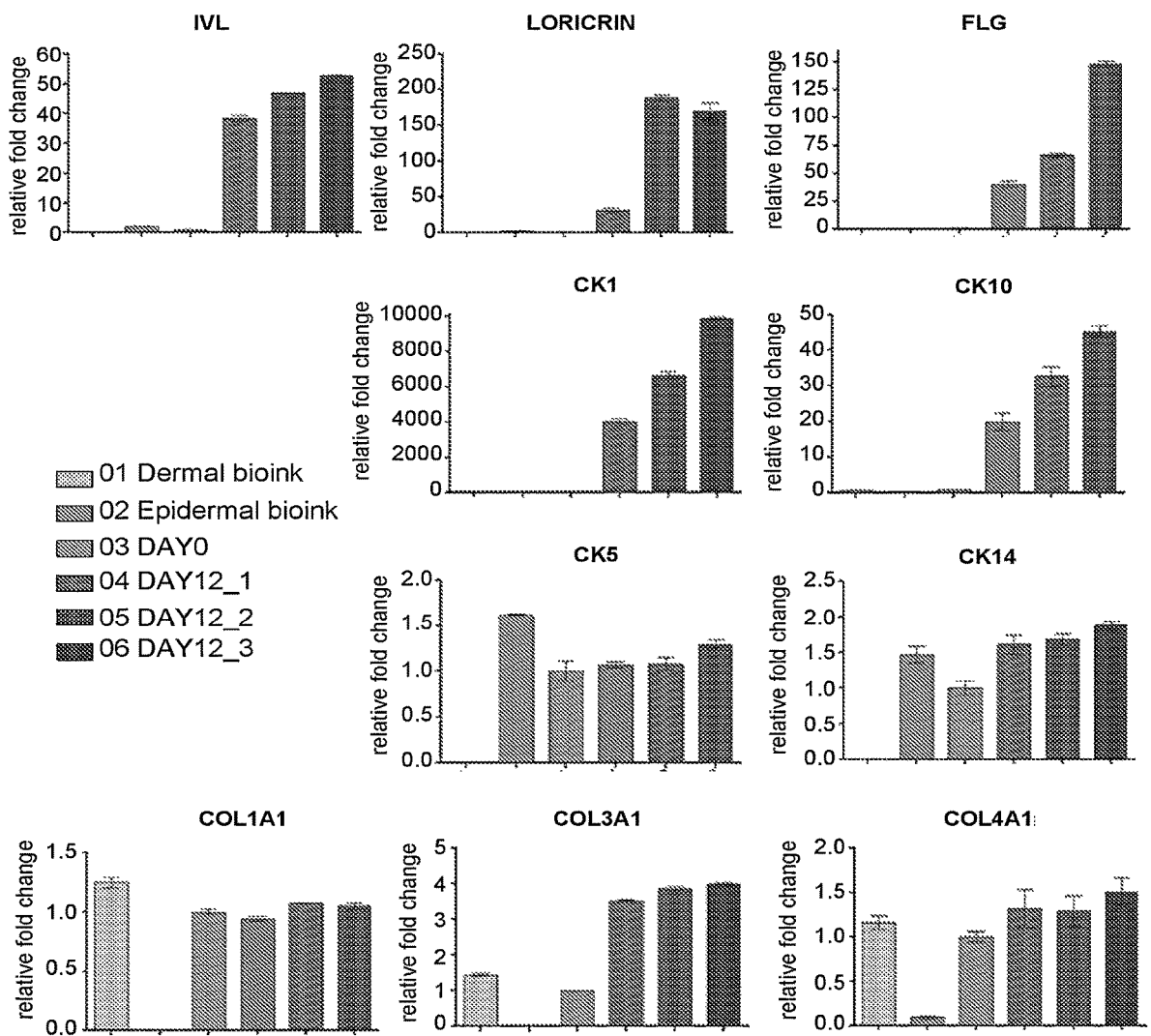
FIG. 9 shows gene expression analysis of bioprinted skin tissue of Example 2 at day 12.
Figure 10:
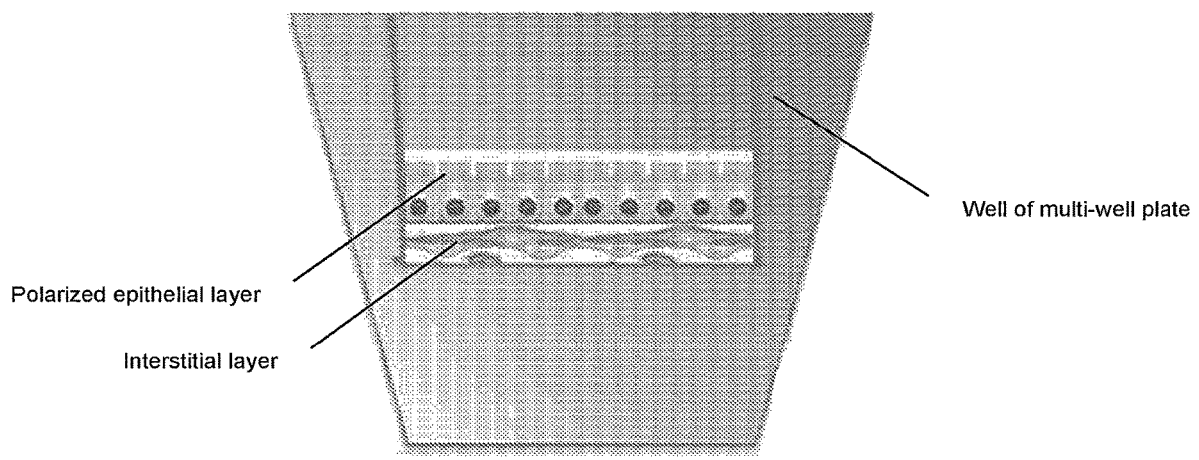
FIG. 10 shows a non-limiting example of a schematic concept diagram; in this case, a schematic concept diagram depicting an interstitial layer topped with a polarized epithelial monolayer.

Gene expression analysis supports histological findings. Data shows an increase in mid epidermal differentiation markers CK1, CK10, and later markers IVL, Loricrin, and at day 12 compared to day 0. Gene expression also shows that collagen I and 4 levels are maintained over the time course of the experiment, while collagen 3 levels increase suggesting the dermal layer remains viable and functional (FIG. 9).

A number of surprising results were determined from this; for example, that epidermal paste can stratify into a distinct layered architecture. Current 3D skin models rely on differentiation of a single keratinocyte monolayer over an extended period of time to achieve this. Here we show that stratification is possible to achieve with a paste. The thickness of the paste is greater than a monolayer where the monolayer is approximately 18-20 microns) and shows that cells can self-organize within the paste and differentiate as layers. Also, we show that the keratinocyte paste printed directly onto the transwell surface without the presence of dermal tissue did not organize into stratified layers. Staining for the same differentiation markers shows mixed expression with no defined layers or distinct cell morphology. This unexpected finding indicates that the dermal layer directs differentiation and/or stratification of the epidermal keratinocytes, and that there is a uniqueness to the combination of dermal and epidermal cells that is not present in the epidermal cells alone. 3) The extent of the layered architecture observed in the tissues comprised of both epidermal and dermal cells including the staining of the CK5-positive basal layer which is limited to a defined region at the base of the epidermal layer similar to native human skin. The layered architecture also includes a CK10 positive (FIG. 8C) spinous and granular keratinocytes in mid stages differentiation and with a morphologically distinct cornified layer of keratinocytes visible by H&E and Trichrome staining above that (FIGS. 8A and D respectively).

Figure 8:
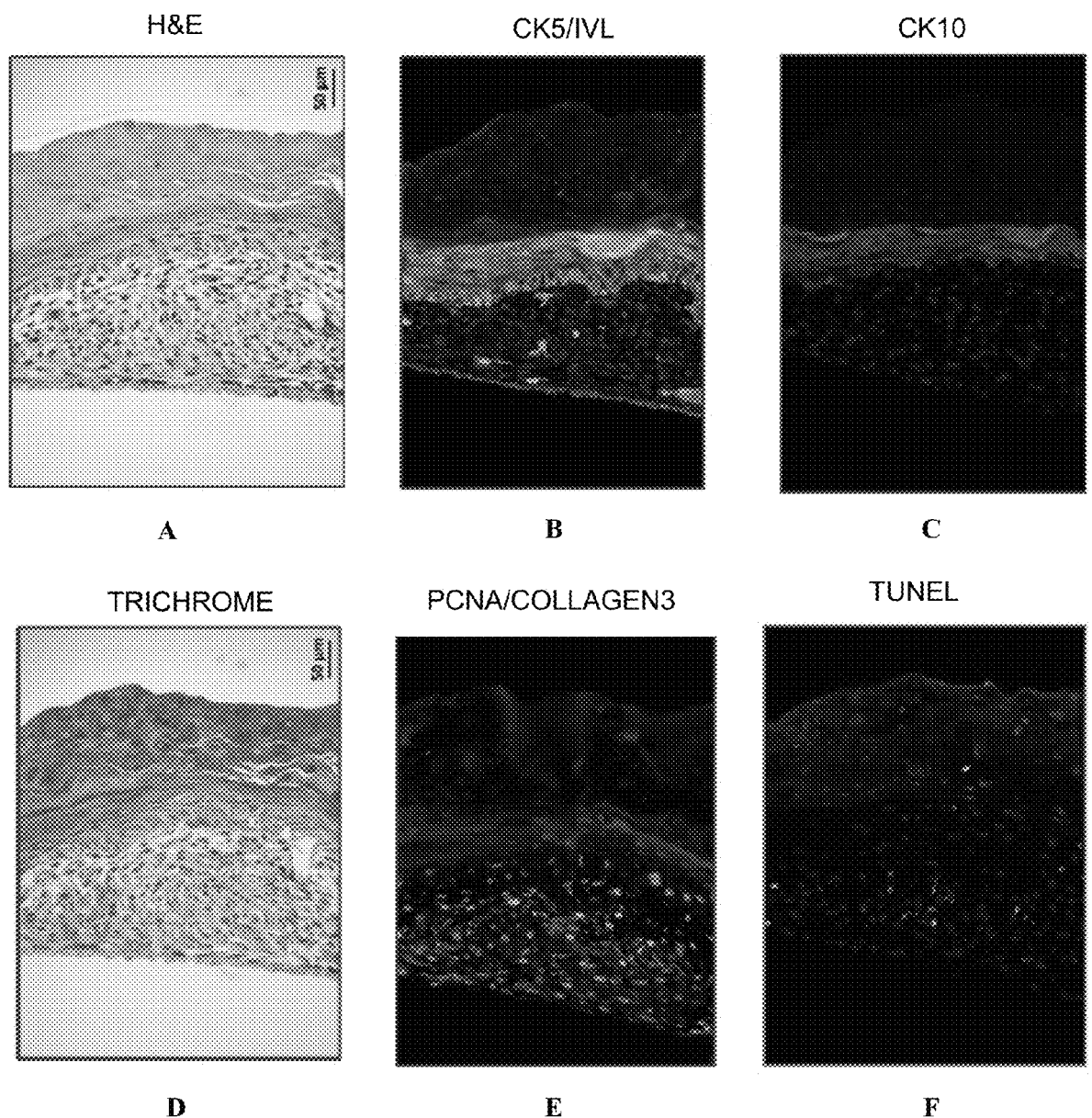
FIG. 8 histological analysis of bioprinted skin tissue of Example 2 at day 12. Shown is H&E staining (A), staining for CK5/IVL (B), CK10 (C), trichrome stain (D), PCNA and Collagen (E) and TUNEL staining (F).

A noteworthy advantage to this approach is the appearance of the dermal layer. H&E staining shows that the dermal fibroblasts do not form a thin sheet as in earlier examples 1 and 2, but a thicker structure. Collagen deposition, which is a key indicator of normal fibroblast function in the dermis, can be seen by both trichrome staining (blue color) and by immunofluorescent staining for collagen 3 (red) in between dermal cells (FIG. 8).

Example 3—Incubation Below 37° C. Improves Kidney Tissue Formation

The interstitial layer of the renal proximal tubule model is composed of renal fibroblasts and HUVECs in NOVOGEL. To reduce the thickness and cellularity of the interstitial layer, the cell ratio was changed to 50% fibroblasts/50% HUVEC the concentration of the cells was 125 million cells/mL. Attempts to fabricate tissues using these cell ratios were hampered by a propensity of the tissues to "ball up," preventing the sort of thin, spread out interstitial layer that is ideal. To assist in maintenance of construct shape following bioprinting, tissues were incubated at 30° C. for 3 days following printing to slow the rate of NOVOGEL dissipation.

Figure 14:
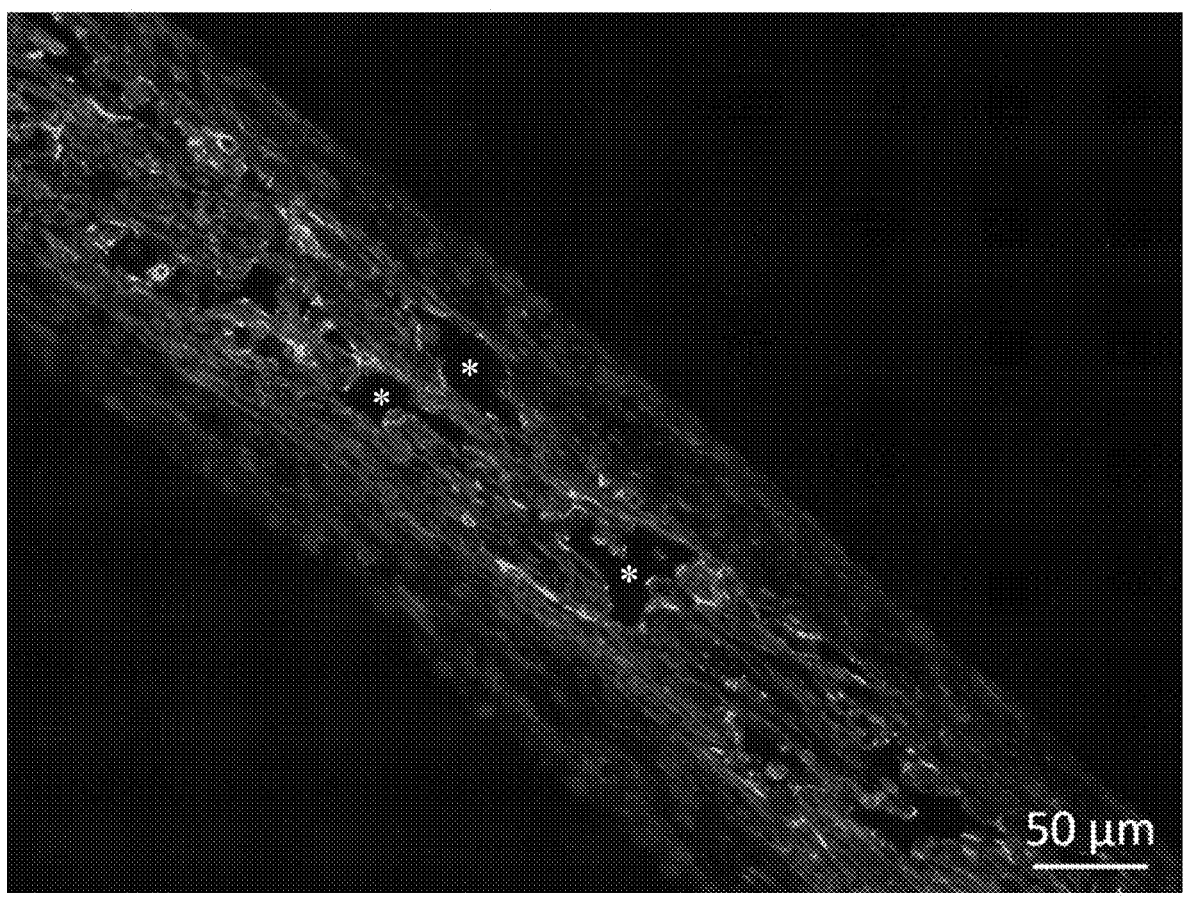
FIG. 14 shows that extensive endothelial cell networks are observed in 3D bioprinted renal tissue constructs from Example 3. Staining for CD31, (endothelial cells, green) and TE7 (fibroblasts, red) are shown. Networks with putative lumens lined with endothelial cells are marked with (*).
Figure 15:
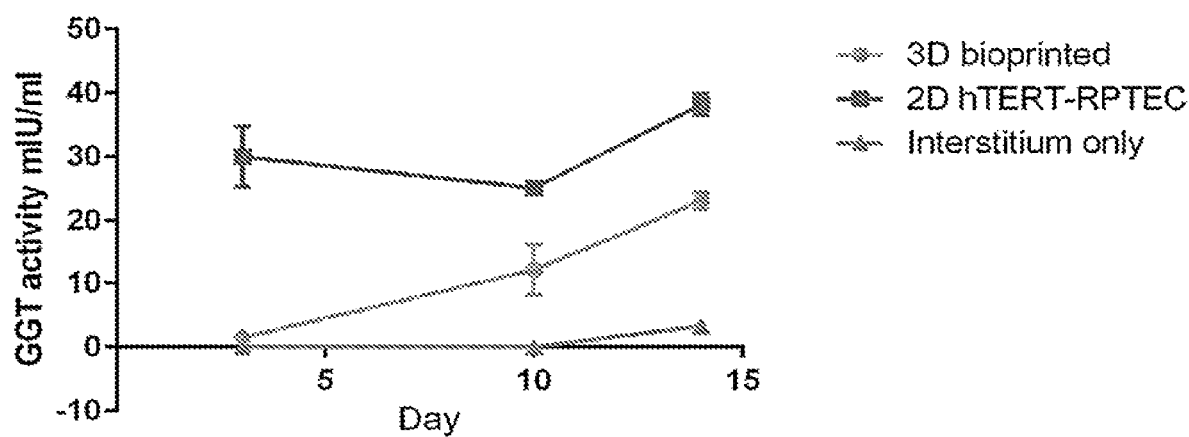
FIG. 15 shows GGT activity in 3D bioprinted renal tissue from Example 3 and in 2D hTERT-RPTEC cells but not in interstitial cells alone.

The results show a tissue that better retains its overall dimensions (FIGS. 11C and D) after 30° C. incubation, when compared to 37° C. incubation (FIGS. 11A and B), and allows the cells to proliferate and secrete ECM to replace the NOVOGEL material as a binding agent (FIG. 11B). Following this maturation step, tissues can be shifted to 37° C. for the addition of epithelial cells to the structure, with no loss of tissue features or viability as a result of the culture time at 30° C. H&E staining is shown (FIG. 12A), and brush borders are indicated (FIG. 13 A, arrows). Trichrome staining indicates collagen secretion (FIGS. 12B, blue and 13B, arrows), and CD31 staining indicates the presence of HUVEC networks (FIG. 14, asterisks). Bioprinted tissues demonstrated γ-glutamyl-transferase activity which increases over time in culture, which is indicative of a functioning epithelial layer (FIG. 15). Considering that the kidney is a fully internal structure normally kept at 37° C., it is unexpected that the culture time at 30° C. would result in a tissue with the desired structural and functional characteristics.

Figure 17:
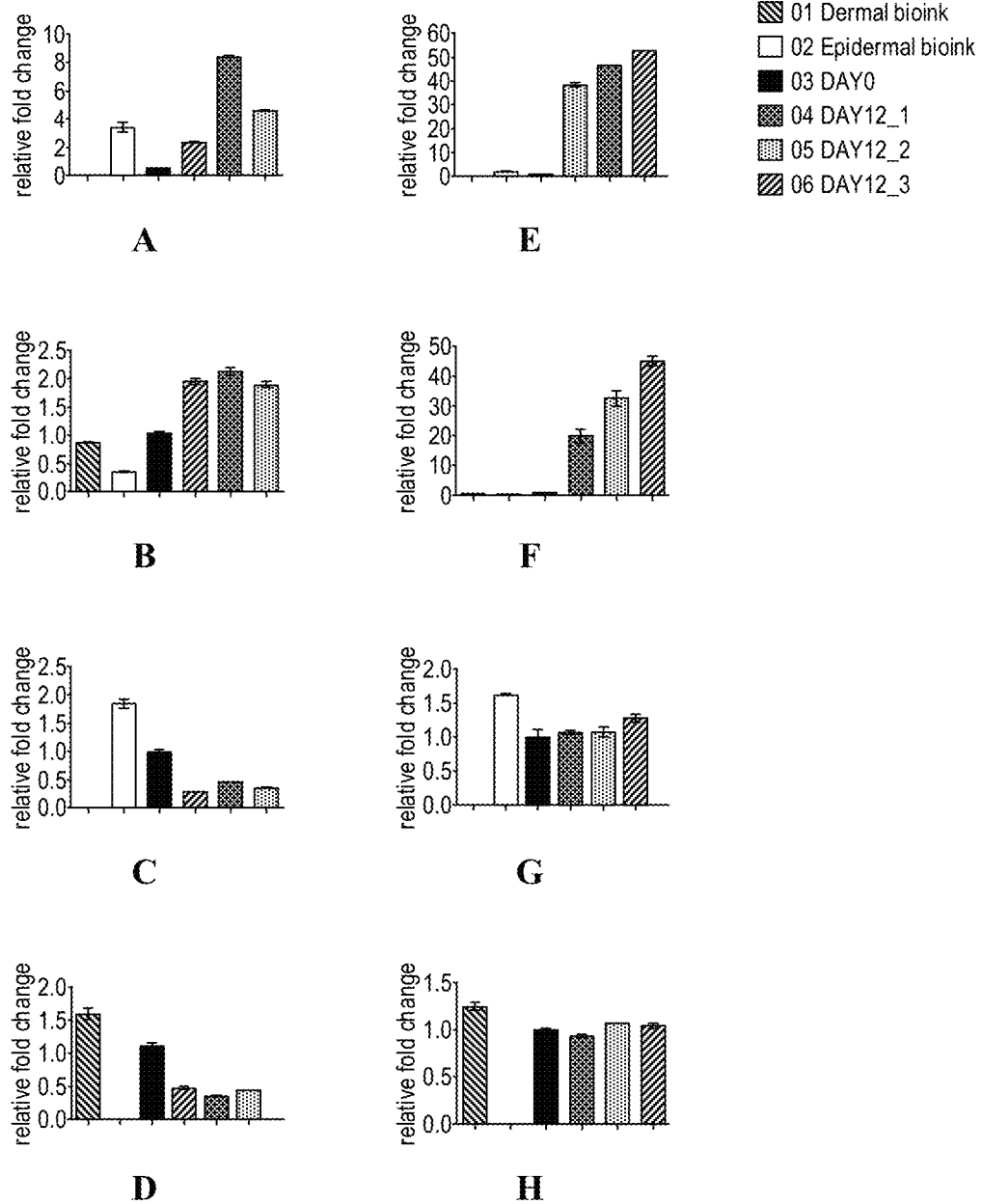
FIG. 17 shows gene expression data comparing skin tissue fabricated with a 4° C. hypothermic hold and incubation at 30° C. for 5 days, (E, F, G, and H) versus skin tissue fabricated without these techniques (A, B, C, and D). Genes assayed by qPCR were: Involucrin (IVL) (A and E), CK10 (B and F), CK5 (C and G) and Col1a1 (D and H).
Figure 18:
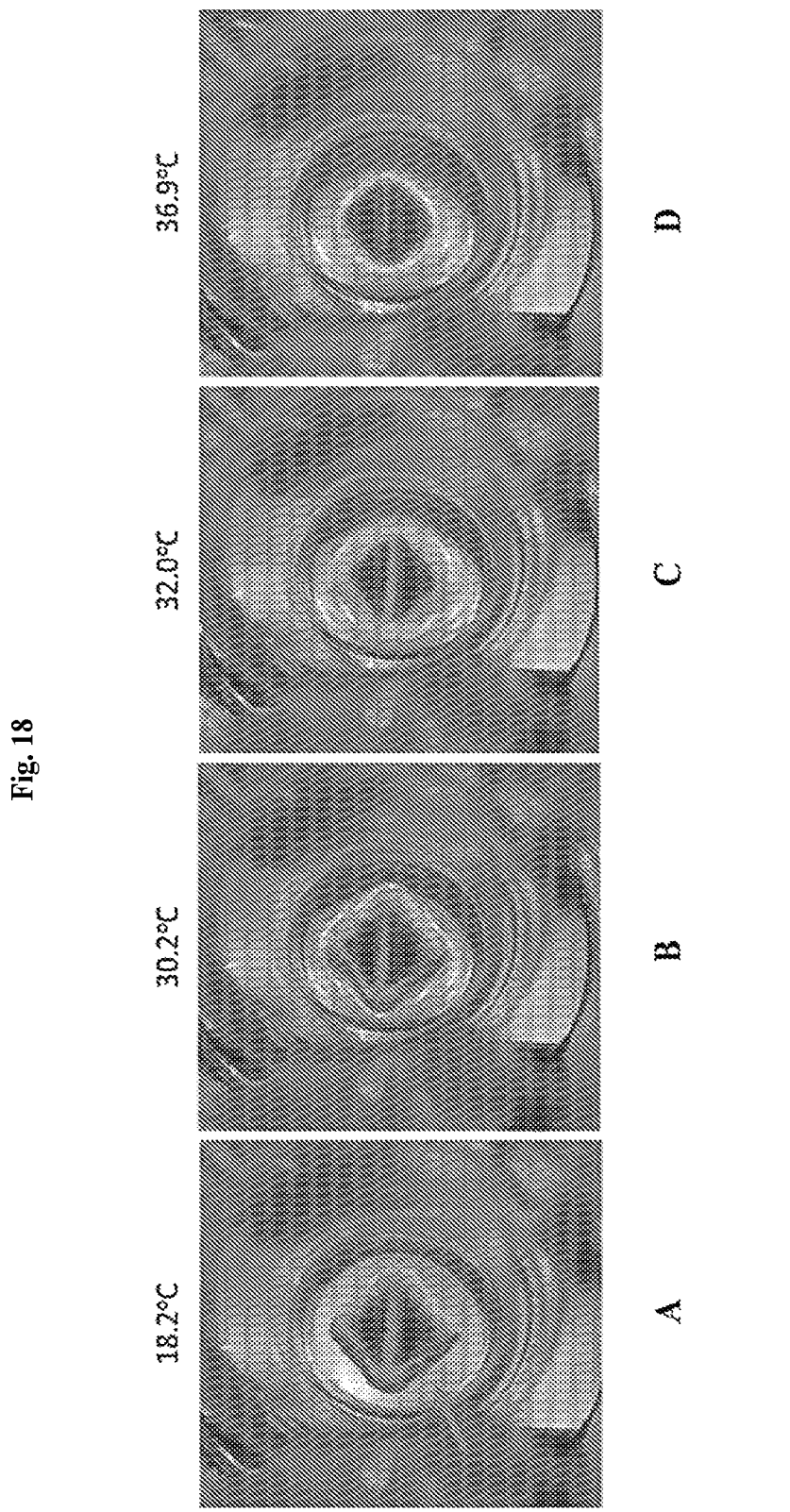
FIG. 18 shows photographs showing the temperature dependence of the viscosity of cellular bio-ink at 18.2° C. (A), 30.2° C. (B), 32.0° C. (C), and 36.9° C. (D). Bio-ink that forms and is distinctly visible on the outer edge of liver tissue (clear diamond bordering the dark triangles indicated by an arrow) at 18.2° C. (A) is maintained at 30.2° C. (B). The tissue edges break down at 32.0° C. (C) and completely disappear at 36.9° C. (D).

Example 4—Comparison of Skin Tissue Fabricated Using a 4° C. Hypothermic Hold and a 30° C. Incubation Tissues that are fabricated using the methods disclosed here display quantitative and qualitative improvements. Referring to FIG. 16 skin tissue fabricated using a 4° C. hold with a 30° C. incubation step for 5 days exhibit reduced apoptosis (FIG. 16B), as indicated by TUNEL staining, when compared to tissue fabricated without these techniques (FIG. 16A). Likewise, when tissue is assayed for gene expression differentiation markers IVL, CK10, CK5 and Col1a1 are elevated in tissue fabricated using a 4° C. hold with a 30° C. incubation step for 5 days (FIGS. 17E, F, G, and H), when compared to tissue fabricated without these techniques (FIGS. 17A, B, C, and D). Taken together FIG. 16 and FIG. 17 show that tissue fabricated using a hypothermic hold and incubation below 37° C. results in tissues with increased viability and differentiation.

Example 5—Incubation Below 37° C. Prevents Breakdown at Tissue Edges

Liver tissues comprising primary human hepatocytes, endothelial cells, and stellate cells were bioprinted and immediately placed in an incubator under varying temperatures (18.2° C., 30.2° C., 32.0° C., and 36.9° C.) and imaged.

FIG. 18A-D are photographs showing the temperature dependence of the viscosity of cellular bio-ink at 18.2° C. (A), 30.2° C. (B), 32.0° C. (C), and 36.9° C. (D). Bio-ink that forms and is distinctly visible on the outer edge of liver tissue (clear diamond bordering the dark triangles indicated by an arrow) at 18.2° C. (A) is maintained at 30.2° C. (B). The tissue edges break down at 32.0° C. (C) and completely disappear at 36.9° C. (D). Therefore, incubation at 36.9° C. does not produce liver tissue having the desired structural and functional characteristics.

What is claimed is:

1. A method of fabricating a three-dimensional, engineered, biological tissue, the method comprising:
    a) preparing a bio-ink comprising living cells, wherein the bio-ink is a viscous liquid, a semi-solid, or a solid;
    b) depositing the bio-ink onto a surface by extrusion bioprinting to form a structure;
    c) exposing the bio-ink to a hypothermic hold of greater than or equal to 2° C., but less than 10° C. after bioprinting; and
    d) incubating the bio-ink at a temperature of greater than or equal to 18° C., but less than 37° C. after the hypothermic hold;
wherein the bio-ink is not exposed to any ionic, chemical, photo or physical cross-linker during the incubation at a temperature of greater than or equal to 18° C., but less than 37° C., and wherein the shape of the structure is maintained during the hypothermic hold and the incubating.

2. The method of claim 1, wherein apoptosis in a bioprinted tissue is reduced by fabrication using said method, in comparison to an engineered tissue not fabricated by said method.

3. The method of claim 1, wherein the bio-ink is not exposed to any ionic, chemical, photo or physical cross-linker during the hypothermic hold of greater than or equal to 2° C., but less than 10° C. after bioprinting.

4. The method of claim 1, wherein the bio-ink further comprises a test substance, wherein the test substance is a substance under evaluation for its ability to elicit a change in a tissue compared to a tissue not treated with said substance.

5. The method of claim 1, wherein the bio-ink consists essentially of a single human cell-type.

6. The method of claim 1, wherein the biological tissue is free of a pre-formed scaffold.

7. The method of claim 1, wherein the method does not comprise the use of ionic, chemical, photo, or physical cross-linker.

8. The method of claim 1, wherein the bio-ink comprises renal fibroblasts and human umbilical vein endothelial cells (HUVECs).

9. The method of claim 1, wherein the hypothermic hold is no more than 60 minutes.

10. A method of fabricating a three-dimensional, engineered, biological tissue, the method comprising:
   a) preparing a plurality of bio-inks comprising living cells, wherein the bio-ink is a viscous liquid, a semi-solid, or a solid;
   b) depositing a first bio-ink onto a surface by extrusion bioprinting;
   c) incubating the first bio-ink at a temperature of greater than or equal to 18° C., but less than 37° C.;
   d) depositing a second bio-ink onto a surface by extrusion bioprinting; and
   e) incubating the plurality of bio-inks at a temperature of greater than or equal to 18° C., but less than 37° C.;
further comprising: exposing the first bio-ink to a hypothermic hold of greater than or equal to 2° C., but less than 10° C. after bioprinting the first bio-ink and before incubating the first bio-ink, exposing the plurality of bio-inks to a hypothermic hold of greater than or equal to 2° C., but less than 10° C. after bioprinting the second bio-ink and before incubating the plurality of bio-inks, or both; wherein the first bio-ink, the plurality of bio-inks, or both are not exposed to any ionic, chemical, photo or physical cross-linker during the incubating at a temperature of greater than or equal to 18° C., but less than 37° C., wherein the depositing of the first bio-ink and the second bio-ink forms a structure, and wherein the shape of the structure is maintained during the hypothermic hold and the incubatings.

11. The method of claim 10, wherein apoptosis in a bioprinted tissue is reduced by fabrication using said method, in comparison to an engineered tissue not fabricated by said method.

12. The method of claim 10, wherein the first bio-ink, the plurality of bio-inks, or both are not exposed to any ionic, chemical, photo or physical cross-linker during a hypothermic hold of greater than or equal to 2° C., but less than 10° C. after bioprinting.

13. The method of claim 10, wherein at least one of the first or second bio-inks or both bio-inks comprise a test substance, wherein the test substance is a substance under evaluation for its ability to elicit a change in a tissue compared to a tissue not treated with said substance.

14. The method of claim 10, wherein the biological tissue is free of a pre-formed scaffold.

15. The method of claim 10, wherein the method does not comprise the use of ionic, chemical, photo, or physical cross-linker.

16. The method of claim 10, wherein the bio-ink comprises renal fibroblasts and HUVECs.

17. The method of claim 10, wherein the hypothermic hold is no more than 60 minutes.

* * * * *